United States Patent [19]

Misslitz et al.

[11] Patent Number: 5,190,573
[45] Date of Patent: Mar. 2, 1993

[54] CYCLOHEXENONE OXIME ETHERS, THEIR PREPARATION AND THEIR USE AS HERBICIDES

[75] Inventors: Ulf Misslitz, Neustadt; Norbert Meyer, Ladenburg; Juergen Kast, Boehl-Iggelheim; Norbert Goetz, Worms; Albrecht Harreus, Ludwigshafen; Bruno Wuerzer, Otterstadt; Helmut Walter, Obrigheim; Karl-Otto Westphalen, Speyer; Matthias Gerber, Mutterstadt, all of Fed. Rep. of Germany

[73] Assignee: BASF Aktiengesellschaft, Ludwigshafen, Fed. Rep. of Germany

[21] Appl. No.: 697,050

[22] Filed: May 8, 1991

[30] Foreign Application Priority Data

May 9, 1990 [DE] Fed. Rep. of Germany ....... 4014986
Oct. 20, 1990 [DE] Fed. Rep. of Germany ....... 4033423

[51] Int. Cl.[5] .................. A01N 43/16; C07D 309/06
[52] U.S. Cl. .................................... 504/292; 549/414; 549/426; 549/21; 549/28; 549/14; 549/372; 549/376; 549/378; 549/379; 549/417; 549/419; 549/491; 549/61; 549/63; 549/64; 549/65; 549/71; 549/72; 549/75; 549/77; 549/474; 549/471; 549/480; 549/481; 549/484; 549/495; 549/13; 549/37; 549/38; 549/39; 549/60; 549/448; 549/451; 549/479; 546/200; 546/283; 546/284; 548/517; 548/527; 548/531; 548/543; 548/558; 548/561; 504/344; 504/289; 504/294; 504/295; 504/290; 504/288; 504/310; 504/339; 504/337; 504/322; 504/315; 504/244; 504/254; 504/260

[58] Field of Search ............ 549/13, 37, 38, 39, 549/59, 60, 448, 451, 479, 414, 426, 21, 22, 28, 14, 372, 376, 378, 379, 417, 419, 491, 61, 63, 64, 65, 71, 72, 75, 77, 474, 471, 480, 481, 484, 495; 71/88, 90, 91, 123, 94, 95, 105, 93; 564/256; 548/527, 517, 531, 543, 558, 561; 546/283, 284, 200

[56] References Cited

U.S. PATENT DOCUMENTS

| | | | |
|---|---|---|---|
| 4,440,566 | 4/1984 | Lou | 71/98 |
| 4,624,696 | 11/1986 | Keil et al. | 71/88 |
| 4,812,160 | 3/1989 | Jahn et al. | 549/387 |
| 4,880,456 | 11/1989 | Kolassa et al. | 71/88 |
| 5,022,914 | 6/1991 | Klast et al. | 548/205 |
| 5,034,047 | 7/1991 | Kolassa et al. | 549/59 |

FOREIGN PATENT DOCUMENTS

| | | |
|---|---|---|
| 2001842 | 5/1990 | Canada . |
| 0080301 | 6/1983 | European Pat. Off. . |
| 0125094 | 11/1984 | European Pat. Off. . |
| 0172551 | 2/1986 | European Pat. Off. . |
| 0218233 | 10/1986 | European Pat. Off. . |
| 0332076 | 3/1989 | European Pat. Off. . |

Primary Examiner—Carolyn Elmore
Assistant Examiner—Mark W. Russell
Attorney, Agent, or Firm—Herbert B. Keil

[57] ABSTRACT

Cyclohexenone oxime ethers

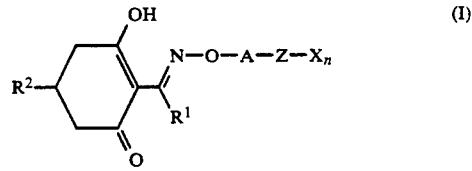

(I)

where
$R^1$ is alkyl;
A is substituted or unsubstituted alkylene or alkenylene, where methylene is replaced by an oxygen atom, a sulfur atom, a sulfoxyl group, a sulfonyl group or $-NR^a-$,
Z is phenyl or a 5- or 6-membered heteroaromatic structure;
X is substituted or unsubstituted amino, nitro, cyano, halogen, alkyl, $C_1-C_4$-alkoxy, $C_1-C_4$-alkylthio, $C_1-C_4$-haloalkyl, $C_1-C_4$-haloalkoxy, carboxyl, $C_1-C_4$-alkoxycarbonyl, substituted or unsubstituted benzyloxycarbony or phenyl;
n is 0 to 3, or 1 to 5 where X is halogen;
$R^2$ is alkoxyalkyl or alkylthioalkyl,
  substituted or unsubstituted cycloalkyl or cycloalkenyl,
  a substituted or unsubstituted 5-membered saturated heterocyclic structure with one or two heteroatoms,
  a substituted or unsubstituted 6- or 7-membered heterocyclic structure with 1-2 heteroatoms and 0-2 double bonds,
  a substituted or unsubstituted 5-membered heteroaromatic radical with 1-3 heteroatoms, or
  substituted or unsubstituted phenyl or pyridyl,
and their agriculturally useful salts and esters of $C_1-C_{10}$-carboxylic acids and inorganic acids, processes for their manufacture, and their use as herbicides.

7 Claims, No Drawings

CYCLOHEXENONE OXIME ETHERS, THEIR PREPARATION AND THEIR USE AS HERBICIDES

The present invention relates to novel herbicidal cyclohexenone oxime ethers of the formula I

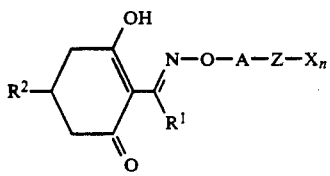

where
$R^1$ is $C_1-C_6$-alkyl;
A is an unsubstituted or $C_1-C_3$-alkyl-substituted $C_3-C_6$-alkylene or $C_4-C_6$-alkenylene chain in which a methylene group is replaced by an oxygen atom, a sulfur atom, a sulfoxyl group, a sulfonyl group or —N(-$R^a$)—, where
$R^a$ is hydrogen, $C_1-C_4$-alkyl, $C_3-C_6$-alkenyl or $C_3-C_6$-alkynyl;
Z is phenyl,
a 5-membered heteroaromatic structure having from one to three hetero atoms selected from the group consisting of three nitrogen atoms and an oxygen or sulfur atom or
a 6-membered heteroaromatic structure having from one to four nitrogen atoms;
X is an amino group —$NR^aR^b$, where
$R^a$ is hydrogen, $C_1-C_4$-alkyl, $C_3-C_6$-alkenyl or $C_3-C_6$-alkynyl and
$R^b$ is hydrogen, $C_1-C_4$-alkyl, $C_3-C_6$-alkenyl, $C_3-C_6$-alkynyl, $C_1-C_6$-acyl or benzoyl, where the aromatic ring may carry from one to three substituents selected from the group consisting of nitro, cyano, halogen, $C_1-C_4$-alkyl, $C_1-C_4$-alkoxy, $C_1-C_4$-alkylthio and $C_1-C_4$-haloalkyl; nitro, cyano, halogen, $C_1-C_4$-alkyl, partially or completely halogenated $C_1-C_4$-alkyl, $C_1-C_4$-alkoxy, $C_1-C_4$-alkylthio, partially or completely halogenated $C_1-C_4$-alkoxy, carboxyl, $C_1-C_4$-alkoxycarbonyl, benzyloxycarbonyl or phenyl, where the aromatic radicals may additionally carry from one to three of the following substituents: nitro, cyano, halogen, $C_1-C_4$-alkyl, partially or completely halogenated $C_1-C_4$-alkyl, $C_1-C_4$-alkoxy, $C_1-C_4$-alkylthio, partially or completely halogenated $C_1-C_4$-alkoxy, carboxyl, $C_1-C_4$-alkoxycarbonyl or benzyloxycarbonyl;
n is from 0 to 3 or from 1 to 5 where Z is halogen;
$R^2$ is $C_1-C_4$-alkoxy-$C_1-C_6$-alkyl or $C_1-C_4$-alkylthio-$C_1-C_6$-alkyl;
$C_3-C_7$-cycloalkyl or $C_5-C_7$-cycloalkenyl, where these groups may carry from one to three substituents selected from the group consisting of $C_1-C_4$-alkyl, $C_1-C_4$-alkoxy, $C_1-C_4$-alkylthio, partially or completely halogenated $C_1-C_4$-alkyl, hydroxyl and halogen;
a 5-membered saturated heterocyclic structure which contains one or two hetero atoms selected from the group consisting of oxygen and sulfur, where the heterocyclic structure may additionally carry from one to three radicals selected from the group consisting of $C_1-C_4$-alkyl, $C_1-C_4$-alkoxy, $C_1-C_4$-alkylthio and partially or completely halogenated $C_1-C_4$-alkyl;
a 6-membered or 7-membered saturated or mono- or diunsaturated heterocyclic structure containing one or two hetero atoms selected from the group consisting of oxygen and sulfur where the heterocyclic structure may additionally carry from one to three radicals selected from the group consisting of hydroxyl, halogen, $C_1-C_4$-alkyl, $C_1-C_4$-alkoxy, $C_1-C_4$-alkylthio and partially or completely halogenated $C_1-C_4$-alkyl;
a 5-membered heteroaromatic structure containing one to three hetero atoms selected from the group consisting of two nitrogen atoms and an oxygen atom or a sulfur atom, where this ring may additionally carry from one to three radicals selected from the group consisting of halogen, cyano, $C_1-C_4$-alkyl, $C_1-C_4$-alkoxy, $C_1-C_4$-alkylthio, partially or completely halogenated $C_1-C_4$-alkyl, $C_2-C_6$-alkenyl, $C_2-C_6$-alkenyloxy, partially or completely halogenated $C_2-C_6$-alkenyl and $C_1-C_4$-alkoxy-$C_1-C_4$-alkyl;
phenyl or pyridyl, where these groups may additionally carry from one to three radicals selected from the group consisting of halogen, nitro, cyano, $C_1-C_4$-alkyl, $C_1-C_4$-alkoxy, $C_1-C_4$-alkylthio, partially or completely halogenated $C_1-C_4$-alkyl, $C_3-C_6$-alkenyloxy, $C_3-C_6$-alkynyloxy and —$NR^aR^b$, where $R^a$ and $R^b$ have the abovementioned meanings, and their agriculturally useful salts and esters of $C_1-C_{10}$-carboxylic acids and inorganic acids.

The novel cyclohexenones I are apparently acidic, ie. they can form simple reaction products, such as salts of alkali metal or alkaline earth metal compounds or enol esters.

The compounds of the formula I may occur in a plurality of tautomeric forms, all of which are embraced by the claim.

Cyclohexenones of the general formula I'

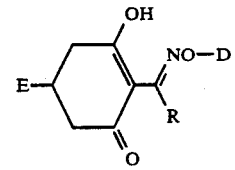

where, inter alia,
D is benzyl and E is 2-ethylthiopropyl (U.S. Pat. No. 4,440,566),
D is benzyl or but-2-enyl and E is a substituted 5-membered hetaryl radical (EP-A 238 021 and EP-A 125 094), D is benzyl or but-2-enyl and E is a substituted phenyl (EP-A 80 301) and
D is but-2-enyl and E is a 5-membered to 7-membered heterocyclic ring having up to two O or S atoms and up to two double bonds (EP-A 218 233),
are described as herbicides in the literature.

It is an object of the present invention to provide compounds which have high selectivity, ie. control undesirable plants without damaging the crops, at a low application rate.

We have found that this object is achieved by the novel cyclohexenone oxime ethers of the formula I, which have a good herbicidal action with respect to undesirable grasses. The compounds are compatible with broad-leaved crops and some of them are compatible with gramineous crops, such as rice.

The cyclohexenones of the formula I can be prepared in a conventional manner from known derivatives of the formula II (EP-A 80 301, EP-A-125 094, EP-A-142 741, U.S. Pat. No. 4,249,937, EP-A 137 174 and EP-A 177 913) and the corresponding hydroxylamines of the formula III (Houben-Weyl, 10/1, page 1181 et seq.) (EP-A 169 521).

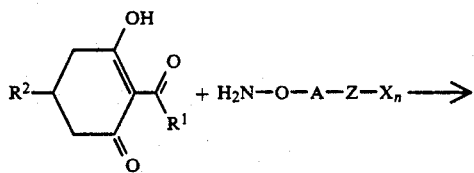

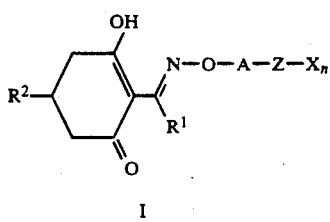

The reaction is advantageously carried out in the heterogeneous phase in a solvent at a sufficient temperature below about 80° C., in the presence of a base, and the hydroxylamine III is used in the form of its ammonium salt.

Examples of suitable bases are carbonates, bicarbonates, acetates, alcoholates or oxides of alkali or alkaline earth metals, in particular sodium hydroxide, potassium hydroxide, magnesium oxide or calcium oxide. Organic bases, such as pyridine or tertiary amines, can also be used. The base is added, for example, in an amount of from 0.5 to 2 mole-equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The desired compound can be isolated, for example, by evaporating down the mixture, partitioning the residue in methylene chloride/water and distilling off the solvent under reduced pressure.

However, the free hydroxylamine base, for example in the form of an aqueous solution, can also be used directly for this reaction; a single-phase or two-phase reaction mixture is obtained, depending on the solvent used for compound II.

Suitable solvents for this variant are, for example, alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds I can be obtained by treating the 3-hydroxy compounds with sodium hydroxide, potassium hydroxide, a sodium alcoholate or a potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts, using ammonia or phosphonium, sulfonium or sulfoxonium hydroxides.

The compounds of the type II can be prepared, for example, from the corresponding cyclohexane-1,3-diones of the formula IV

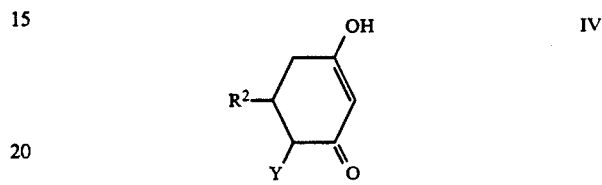

where Y is hydrogen or methoxycarbonyl, by known methods (Tetrahedron Lett. (1975), 2491).

It is also possible to prepare the compounds of the formula II via the enol ester intermediates, which are obtained in the reaction of compounds of the formula IV with acyl chlorides in the presence of bases and are then subjected to a rearrangement reaction with certain imidazole or pyridine derivatives (Japanese Preliminary Published Application 79/063 052).

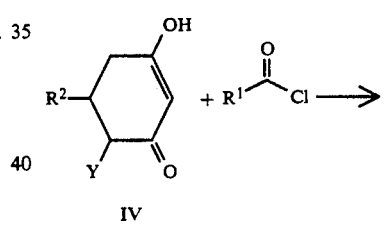

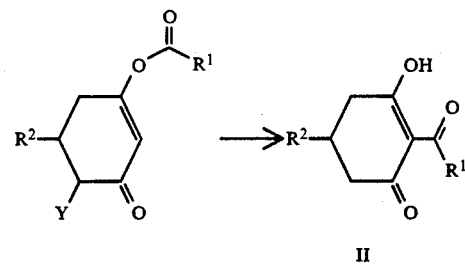

The compounds of the formula IV are obtained by a number of known process steps, starting from known intermediates.

The synthesis of the hydroxylamines III is carried out according to the following reaction scheme:

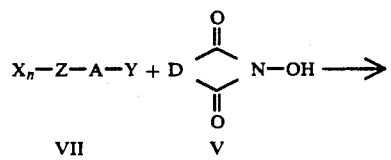

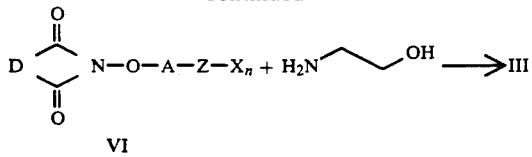

VI

Y = leaving group, eg. halogen such as chlorine, bromine or iodine, or $CH_3SO_2$—O—.

The alkylating agents required for the synthesis of the novel hydroxylamines of the formula III can be prepared by methods known from the literature [cf. DE-A-3 437 919; Tetrahedron Lett. 28 (1979), 2639; Org. Synth. Coll. vol. 1 (1944), 436; DE-A-2 654 646; DE-A-2 714 561; J. Org. Chem. 52 (1987), 3587; DE-A-948 871; DE-A-948 872; J. Med. Chem. 26 (1983), 1570, Synthesis (1983), 675 and J. Org. Chem. 48 (1983), 4970].

VII is coupled to a cyclic hydroximide V, and the resulting protected hydroxylamine derivative VI is cleaved, for example with 2-aminoethanol, to the free hydroxylamine III.

In the cyclic hydroximides V, D is, for example, $C_2$- or $C_3$-alkylene, $C_2$-alkenylene or a 5-membered or 6-membered ring which contains up to 3 double bonds and may contain one nitrogen atom, for example phenylene, pyridinylene, cyclopentylene, cyclohexylene or cyclohexenylene. For example, the following substituents are suitable:

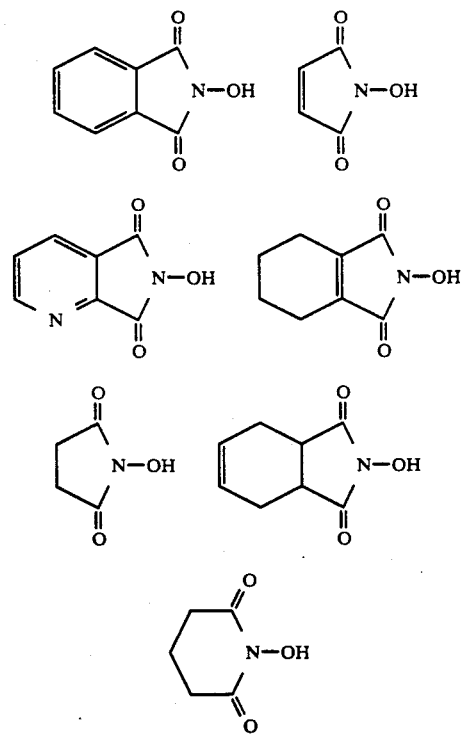

The reaction of the compounds VII with the hydroximides V is advantageously carried out in the presence of a base. Suitable bases are in principle all those which are capable of deprotonating the hydroximides V without attacking the imide system. These are in particular the nonnucleophilic bases. Examples are mineral bases, such as alkali metal and alkaline earth metal carbonates, alkali metal and alkaline earth metal bicarbonates, and organic bases, such as aliphatic, cycloaliphatic and aromatic tertiary amines. Mixtures of these bases can also be used.

Examples of specific compounds are the following bases: sodium carbonate, potassium carbonate, magnesium carbonate, calcium carbonate, barium carbonate, the bicarbonates of these metals, trimethylamine, triethylamine, tributylamine, ethyl diisopropylamine, N,N-dimethylaniline, 4-N,N-dimethylaminopyridine, diazabicyclooctane, diazabicycloundecane, N-methylpiperidine, 1,4-dimethylpiperazine, pyridine, quinoline, bipyridine and phenanthroline. The economical bases sodium carbonate and potassium carbonate are preferred.

The base is generally added in from equivalent amounts to an excess of 5 equivalents, based on the hydroximide. A larger excess is possible but has no additional advantages. The use of a small amount of base is also possible. However, from 1 to 3, in particular from 1 to 2, equivalents, based on the hydroximide V, of a base are preferably used.

The use of nucleophilic bases, for example alkali metal and alkaline earth metal hydroxides, in particular sodium hydroxide and potassium hydroxide, is likewise possible. In this case, it is advantageous to use the base in equivalent amounts, based on the hydroximide V, in order to prevent nucleophilic attack by the hydroxyl ions on the carbonyl function of the imide group.

The starting compounds VII are advantageously reacted with the hydroximides V in a solvent which is inert under the reaction conditions. Examples of advantageous solvents are polar aprotic solvents, such as dimethylformamide, N-methylpyrrolidone, dimethyl sulfoxide, sulfolane and cyclic ureas. The amount of solvent is in general not critical.

The reaction of the starting compounds VII with the hydroximides V can also be carried out using phase transfer catalysis. In this case, solvents which form two phases with water, preferably chlorohydrocarbons, are used. Suitable phase transfer catalysts are the quaternary ammonium and phosphonium salts, polyethylene glycols, polyethylene glycol ethers and crown ethers, which are usually used for such purposes and are described in, for example, Dehmlow et al., Phase Transfer Catalysis, pages 37-45 and pages 86-93, Verlag Chemie, Weinheim 1980. The phase transfer catalysts are advantageously used in amounts of from 1 to 10, preferably from 3 to 5, % by volume, based on the volume of the reaction mixture.

The reaction of the starting compounds VII with hydroximides V is carried out in general at from 0° to 140° C., preferably from 20° to 100° C., in particular from 40° to 80° C. In an advantageous procedure, the hydroximide V is initially taken together with the base in the solvent, and starting material VII is metered into this solution. It may prove advantageous if the hydroximide is added at a lower temperature, for example from 0° to 50° C., and the reaction mixture is not heated to the actual reaction temperature until after this addition.

When the reaction is complete, water is advantageously added to the cooled reaction mixture, the hydroxylamine derivatives VI formed separating out as crystalline solids or as oils. The hydroxylamine derivatives obtained in this manner can, if desired, be further purified by recrystallization or by extraction.

The hydroxylamine derivatives VI can be temporarily stored or converted immediately into the hydroxylamine derivatives III having a free amino group. This conversion can be carried out by conventional methods, as described in, for example, DE-A 36 15 973 and the publications cited therein. The process according to DE-A 36 15 973, in which the hydroxylamine derivatives III are liberated by means of ethanolamine, is preferably used. Liberation of the hydroxylamine derivatives III with the aid of other bases, such as aqueous mineral bases, with amines, hydrazines or hydroxylamines or by means of aqueous acids is also possible.

The hydroxylamine derivatives III can be isolated from the reaction mixtures obtained in this process by conventional methods of working up, for example by extraction or by crystallization. To increase the tendency of these hydroxylamine derivatives to crystallize, it may often be necessary to convert them into their salts with mineral acids or organic acids. For this purpose, in general dilute solutions of these acids are reacted with the hydroxylamine derivatives, advantageously in equivalent amounts. As in the case of the hydroxylamine derivatives having a free amino group, the resulting hydroxylammonium salts can be further processed directly to the herbicides of the formula I or, if desired, can also be stored.

With regard to the biological activity, preferred cyclohexenones of the formula I are those in which the substituents have the following meanings:

$R^1$ is alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular ethyl or propyl;

A is alkylene or alkenylene in which a methylene group has been replaced by an oxygen atom, a sulfur atom, a sulfoxyl group, a sulfonyl group or —N($R^a$)—, such as 3-oxapropylene, 3-azapropylene, 3-thiapropylene, 3-thiapropylene-3-oxide, 3-thiapropylene-3,3-dioxide, 3-oxabutylene, 3-azabutylene, 3-thiabutylene, 3-thiabutylene-3-oxide, 3-thiabutylene-3,3-dioxide, 4-oxabutylene, 4-azabutylene, 4-thiabutylene, 4-thiabutylene-4-oxide, 4-thiabutylene-4,4-dioxide, 4-oxabut-2-enylene, 4-azabut-2-enylene, 4-thiabut-2-enylene, 3-oxapentylene, 3-azapentylene, 3-thiapentylene, 3-thiapentylene-3-oxide, 3-thiapentylene-3,3-dioxide, 4-oxapentylene, 4-azapentylene, 4-thiapentylene, 4-thiapentylene-4-oxide, 4-thiapentylene-4,4-dioxide, 5-oxapentylene, 5-azapentylene, 5-thiapentylene, 5-thiapentylene-5-oxide, 5-thiapentylene-5,5-dioxide, 5-oxapent-3-enylene, 5-azapent-3-enylene, 5-thiapent-3-enylene, 3-oxahexylene, 3-azahexylene, 3-thiahexylene, 3-thiahexylene-3-oxide, 3-thiahexylene-3,3-dioxide, 4-oxahexylene, 4-azahexylene, 4-thiahexylene, 4-thiahexylene-4-oxide, 4-thiahexylene-4,4-dioxide, 5-oxahexylene, 5-azahexylene, 5-thiahexylene, 5-thiahexylene-5-oxide, 5-thiahexylene-5,5-dioxide, 6-oxahexylene, 6-azahexylene, 6-thiahexylene, 6-thiahexylene-6-oxide, 6-thiahexylene-6,6-dioxide, 6-oxahex-4-enylene, 6-axahex4-enylene or 6-thiahex-4-enylene, particularly preferably 3-oxapropylene, 3-oxabutylene or 4-oxabutylene;

$R^a$ is hydrogen; alkyl, such as methyl, ethyl, propyl, 1-methylethyl, butyl, 1-methylpropyl, 2-methylpropyl or 1,1-dimethylethyl, in particular methyl or ethyl;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,2-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl or 2-butenyl;

alkynyl, such as 2-propynyl, 2-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl;

Z is phenyl, 5-membered hetaryl, such as furanyl, pyrrolyl, thienyl, imidazolyl, pyrazolyl, isoxazolyl, oxazolyl, isothiazolyl, thiazolyl, oxadiazolyl, thiadiazolyl or triazolyl, in particular furanyl or thienyl or 6-membered hetaryl, such as pyridyl, pyridazyl, pyrimidyl, pyrazyl, triazyl or tetrazyl, in particular pyridyl or pyrimidyl;

X is nitro, cyano, halogen, such as fluorine, chlorine, bromine or iodine, in particular fluorine or chlorine, alkyl, such as methyl, ethyl, propyl, 1-methylethyl, butyl, 1-methylpropyl, 2-methylpropyl or 1,1-dimethylethyl, in particular methyl or 1,1-dimethylethyl, alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy, carboxyl, alkoxycarbonyl, such as methoxycarbonyl, ethoxycarbonyl, propoxycarbonyl, 1-methylethoxycarbonyl, butoxycarbonyl or 1,1-dimethylethoxycarbonyl, in particular methoxycarbonyl, ethoxycarbonyl or 1,1-dimethylethoxycarbonyl, especially methoxycarbonyl, or benzyloxycarbonyl or phenyl, where the aromatic radicals in turn may carry from one to three of the following radicals: nitro, cyano, carboxyl, benzyloxycarbonyl, halogen, as stated in general and in particular for X, alkyl as stated for $R^1$, in particular methyl, ethyl or 1-methylethyl, alkoxy as stated above, in particular methoxy or ethoxy, alkylthio as stated above, in particular methylthio, haloalkyl as stated above, in particular trifluoromethyl, haloalkoxy as stated above, in particular difluoromethoxy or trifluoromethoxy and/or alkoxycarbonyl as stated above, in particular methoxycarbonyl or ethoxycarbonyl;

an amino group $-NR^aR^b$, where $R^a$ is hydrogen, alkyl, alkenyl or alkynyl as stated in general and in particular for A and $R^b$ is hydrogen, alkyl, alkenyl or alkynyl as stated in general and in particular for $R^a$, or is acyl, such as acetyl, propionyl, butyryl, 2-methylpropionyl, pentanoyl, 2-methylbutyryl, 3-methylbutyryl, 2,2-dimethylpropionyl, hexanoyl, 2-methylpentanoyl, 3-methylpentanoyl, 4-methylpentanoyl, 2,2-dimethylbutyryl, 2,3-dimethylbutyryl, 3,3-dimethylbutyryl or 2-ethylbutyryl, in particular acetyl or propionyl, or benzoyl, where the aromatic radical may carry from one to three of the following radicals: nitro, cyano, carboxyl, benzyloxycarbonyl, halogen as stated in general and in particular for X, alkyl as stated for $R^1$, in particular methyl, alkoxy as stated above, in particular methoxy or ethoxy, alkylthio as stated above, in particular methylthio, haloalkyl as stated above, in particular trifluoromethyl, haloalkoxy as stated above, in particular difluoromethoxy or trifluoromethoxy, and/or alkoxycarbonyl as stated above, in particular methoxycarbonyl or ethoxycarbonyl;

n is 0, 1, 2 or 3, in particular 0, 1 or 2, or, where Z is halogen, furthermore from 1 to 5. n is preferably 0, 1 or 2. Where there is a plurality of radicals X, the substituents may be identical or different.

$R^2$ is alkyl as stated under X, or pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, which are substituted by one of the alkoxy or alkylthio groups stated under X, preferably in the 1-, 2- or 3-position, in particular 2-ethylthiopropyl, 5-membered heterocycloalkyl, such as tetrahydrofuranyl, tetrahydrothienyl, dioxolanyl, dithiolanyl or oxathiolanyl, in particular tetrahydrofuranyl, tetrahydrothienyl or dioxolanyl, where these rings may carry from one to three of the $C_1$–$C_4$-alkyl, $C_1$–$C_4$-alkoxy, $C_1$–$C_4$-alkylthio and/or $C_1$–$C_4$-haloalkyl groups stated above under X, 5-membered hetaryl, such as pyrrolyl, pyrazolyl, imidazolyl, isoxazolyl, oxazolyl, isothiazolyl, thiazolyl, furanyl or thienyl, in particular isoxazolyl or furanyl, a 6-membered or 7-membered heterocyclic structure, such as tetrahydropyran-3-yl, dihydropyran-3-yl, tetrahydropyran-4-yl, dihydropyran-4-yl, tetrahydrothiopyran-3-yl, dihydrothiopyran-3-yl, tetrahydrothiopyran-4-yl, dihydrothiopyran-4-yl or dioxepan-5-yl, in particular tetrahydropyran-3-yl, tetrahydropyran-4-yl or tetrahydrothiopyran-3-yl, phenyl or pyridyl, where the cyclic radicals may carry from one to three of the alkyl, alkoxy, alkylthio and/or haloalkyl groups stated under X.

The 5-membered heteroaromatic structures $R^2$ may carry the following radicals as substituents: halogen as stated under X, in particular fluorine or chlorine, alkoxyalkyl, such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl or 1-ethoxy-1-methylethyl, in particular methoxyethyl or ethoxyethyl, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular 1-methylethenyl or corresponding alkenyloxy and/or haloalkenyl.

The 6-membered and 7-membered heterocyclic structures may also carry hydroxyl groups in addition to the abovementioned substituents.

In the case of the phenyl and pyridyl radicals, suitable substituents in addition to the abovementioned groups are the following radicals:

alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy or 1-ethyl-2-methyl-2-propenyloxy, in particular 2-propenyloxy or 2-butenyloxy, alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy or 1-ethyl-1-methyl-2-propynyloxy, in particular 2-propynyloxy or 2-butynyloxy;

or —$NR^aR^b$ as stated in general and in particular for X.

Particularly preferred cyclohexenone oxime ethers of the formula I are given in the following tables:

TABLE 1

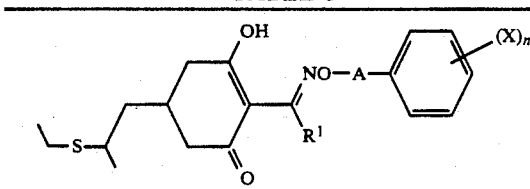

| $R^1$ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |

TABLE 1-continued

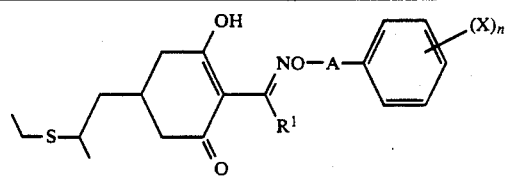

| $R^1$ | A | X | n |
|---|---|---|---|
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 2

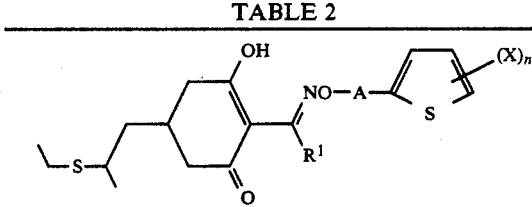

| $R^1$ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-Cl | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |

TABLE 2-continued

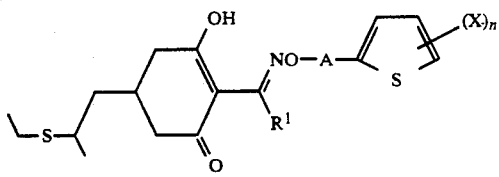

| R¹ | A | X | n |
|---|---|---|---|
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 3

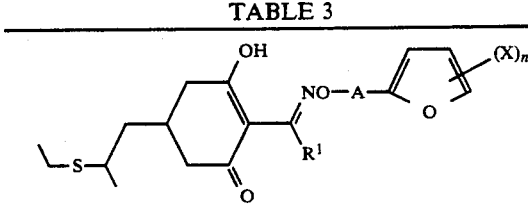

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 4

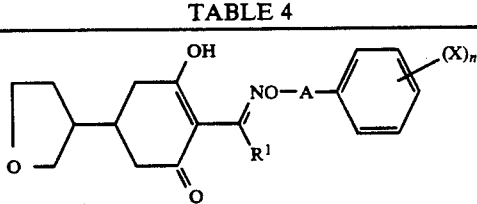

| R¹ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |

TABLE 4-continued

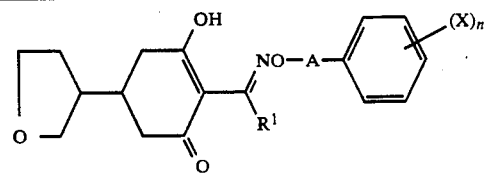

| R¹ | A | X | n |
|---|---|---|---|
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 5

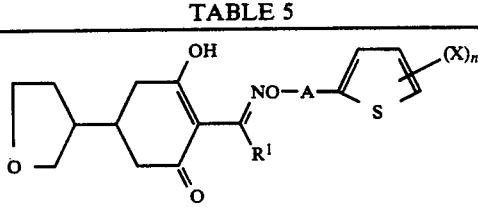

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |

TABLE 5-continued

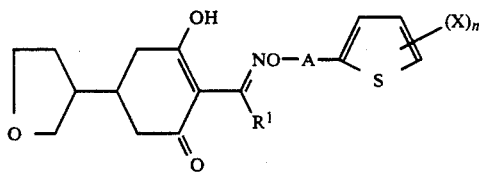

| R¹ | A | X | n |
|---|---|---|---|
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-Cl | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 6

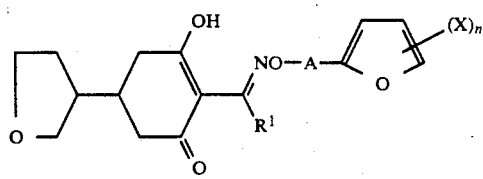

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 7

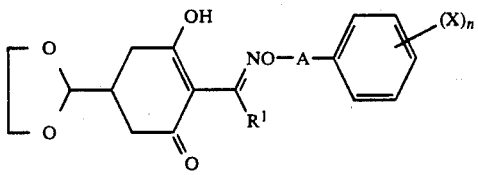

| R¹ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 8

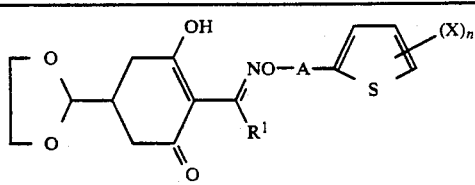

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CL | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 9

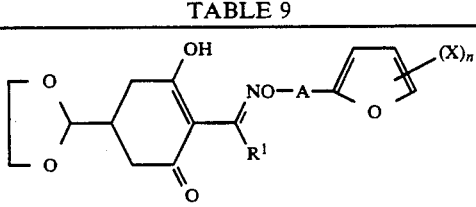

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |

TABLE 9-continued

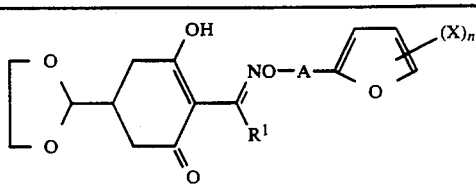

| R¹ | A | X | n |
|---|---|---|---|
| (CH₂)₂CH₃ | CH₂CH₂CH₂CH₂OCH₂ | 5-C₂H₅ | 1 |

TABLE 10

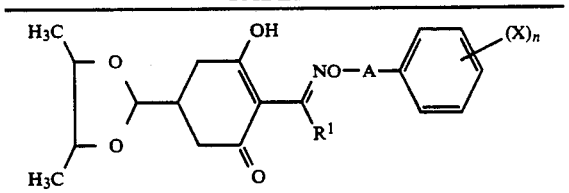

| R¹ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |

TABLE 10-continued

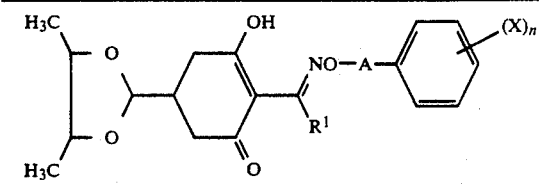

| R¹ | A | X | n |
|---|---|---|---|
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 11

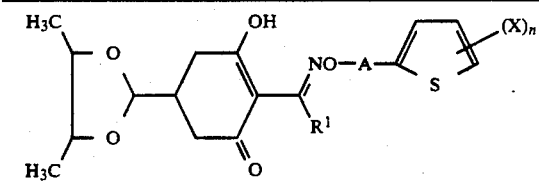

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-Cl | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 12

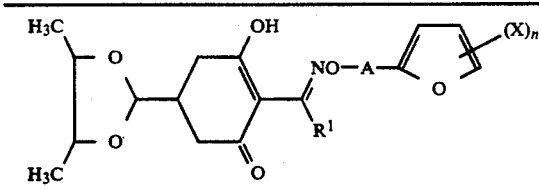

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |

TABLE 12-continued

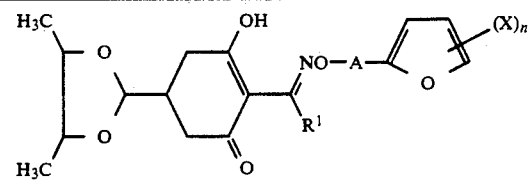

| R¹ | A | X | n |
|---|---|---|---|
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 13

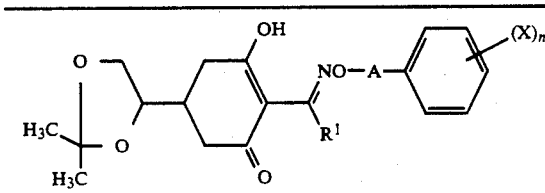

| R¹ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |

TABLE 13-continued

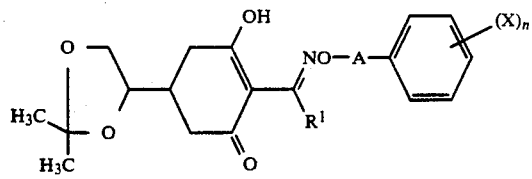

| R¹ | A | X | n |
|---|---|---|---|
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 14

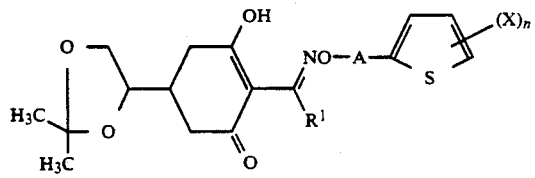

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-Cl | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 15

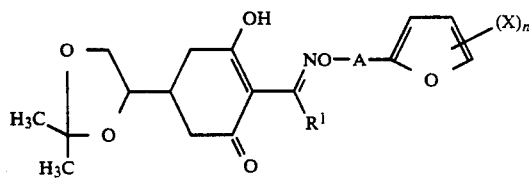

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 16

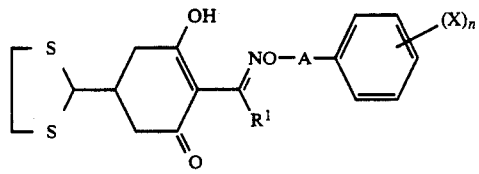

| R¹ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |

TABLE 16-continued

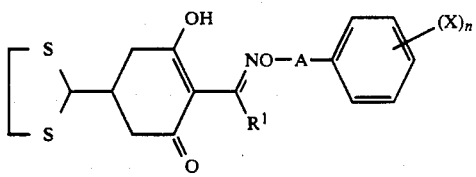

| R¹ | A | X | n |
|---|---|---|---|
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 17

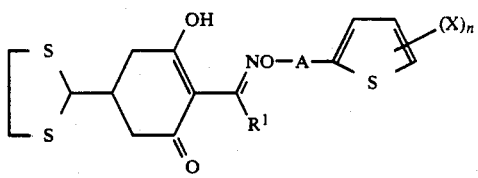

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-Cl | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |

TABLE 17-continued

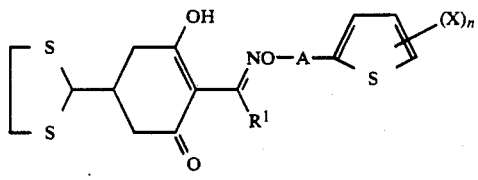

| R¹ | A | X | n |
|---|---|---|---|
| (CH₂)₂CH₃ | CH₂CH₂CH₂CH₂OCH₂ | 5-C₂H₅ | 1 |

TABLE 18

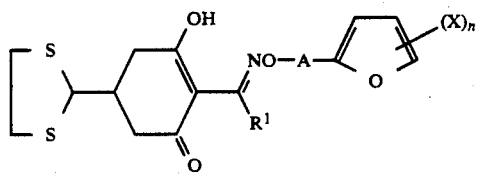

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 19

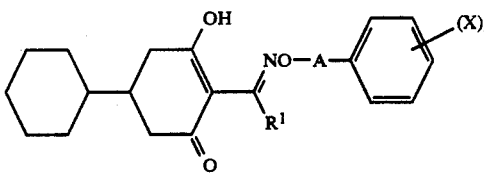

| R¹ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |

TABLE 19-continued

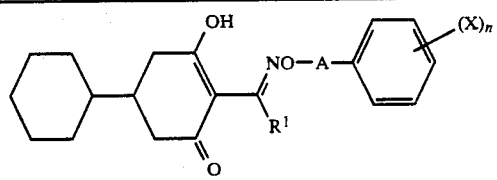

| R¹ | A | X | n |
|---|---|---|---|
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 20

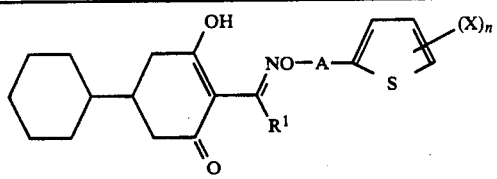

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |

TABLE 20-continued

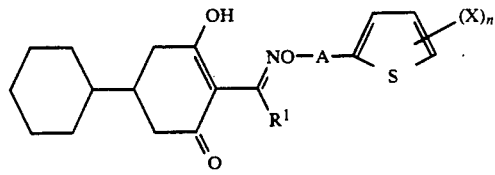

| R¹ | A | X | n |
|---|---|---|---|
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-Cl | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 21

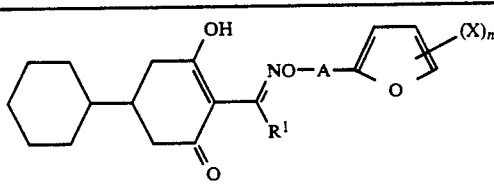

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 22

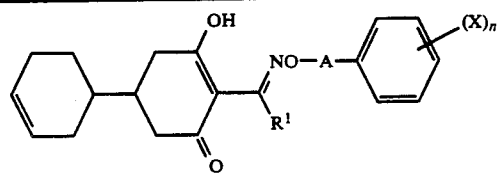

| R¹ | A | X | n |
|---|---|---|---|
| CH₂CH₃ | CH₂CH₂O | — | 0 |
| (CH₂)₂CH₃ | CH₂CH₂O | — | 0 |

TABLE 22-continued

[Structure: cyclohexene-substituted cyclohexenone with OH and C(R¹)=N-O-A-phenyl(X)n group]

| R¹ | A | X | n |
|---|---|---|---|
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₃ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 23

[Structure: cyclohexene-substituted cyclohexenone with OH and C(R¹)=N-O-A-thiophene(X)n group]

| R¹ | A | X | n |
|---|---|---|---|
| CH₂CH₃ | CH₂CH₂OCH₂ | — | 0 |

TABLE 23 -continued

[Structure: cyclohexene-substituted cyclohexenone with OH and C(R¹)=N-O-A-thiophene(X)n group]

| R¹ | A | X | n |
|---|---|---|---|
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂OCH₂CH₂ | — | 0 |
| (CH₂)₂CH₃ | CH₂CH₂OCH₂CH₂ | — | 0 |
| CH₂CH₃ | CH₂CH₂OCH₂CH₂ | 5-Cl | 1 |
| (CH₂)₂CH₃ | CH₂CH₂OCH₂CH₂ | 5-Cl | 1 |
| CH₂CH₃ | CH₂CH₂OCH₂CH₂ | 5-CH₃ | 1 |
| (CH₂)₂CH₃ | CH₂CH₂OCH₂CH₂ | 5-CH₃ | 1 |
| CH₂CH₃ | CH₂CH₂OCH₂CH₂ | 5-C₂H₅ | 1 |
| (CH₂)₂CH₃ | CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 24

[Structure: cyclohexene-substituted cyclohexenone with OH and C(R¹)=N-O-A-furan(X)n group]

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂OCH₂CH₂ | — | 0 |
| (CH₂)₂CH₃ | CH₂CH₂OCH₂CH₂ | — | 0 |
| CH₂CH₃ | CH₂CH₂OCH₂CH₂ | 5-CH₃ | 1 |
| (CH₂)₂CH₃ | CH₂CH₂OCH₂CH₂ | 5-CH₃ | 1 |
| CH₂CH₃ | CH₂CH₂OCH₂CH₂ | 5-C₂H₅ | 1 |
| (CH₂)₂CH₃ | CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 25

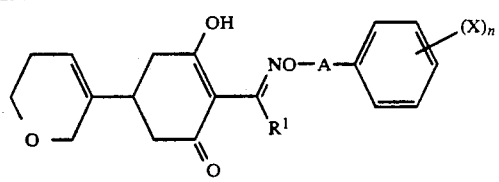

| R¹ | A | X | n |
|---|---|---|---|
| CH$_2$CH$_3$ | CH$_2$CH$_2$O | — | 0 |
| (CH$_2$)$_2$CH$_3$ | CH$_2$CH$_2$O | — | 0 |
| CH$_2$CH$_3$ | CH$_2$CH$_2$O | 2-Cl | 1 |
| (CH$_2$)$_2$CH$_3$ | CH$_2$CH$_2$O | 2-Cl | 1 |
| CH$_2$CH$_3$ | CH$_2$CH$_2$O | 3-Cl | 1 |
| (CH$_2$)$_2$CH$_3$ | CH$_2$CH$_2$O | 3-Cl | 1 |
| CH$_2$CH$_3$ | CH$_2$CH$_2$O | 4-Cl | 1 |
| (CH$_2$)$_2$CH$_3$ | CH$_2$CH$_2$O | 4-Cl | 1 |
| CH$_2$CH$_3$ | CH$_2$CH$_2$O | 2-F | 1 |
| (CH$_2$)$_2$CH$_3$ | CH$_2$CH$_2$O | 2-F | 1 |
| CH$_2$CH$_3$ | CH$_2$CH$_2$O | 3-F | 1 |
| (CH$_2$)$_2$CH$_3$ | CH$_2$CH$_2$O | 3-F | 1 |
| CH$_2$CH$_3$ | CH$_2$CH$_2$O | 4-F | 1 |
| (CH$_2$)$_2$CH$_3$ | CH$_2$CH$_2$O | 4-F | 1 |
| CH$_2$CH$_3$ | CH$_2$CH$_2$O | 3-CF$_3$ | 1 |
| (CH$_2$)$_2$CH$_3$ | CH$_2$CH$_2$O | 3-CF$_3$ | 1 |
| CH$_2$CH$_3$ | CH$_2$CH$_2$CH$_2$O | — | 0 |
| (CH$_2$)$_2$CH$_3$ | CH$_2$CH$_2$CH$_2$O | — | 0 |
| CH$_2$CH$_3$ | CH$_2$CH$_2$CH$_2$O | 4-Cl | 1 |
| (CH$_2$)$_2$CH$_3$ | CH$_2$CH$_2$CH$_2$O | 4-Cl | 1 |
| CH$_2$CH$_3$ | CH$_2$CH$_2$CH$_2$O | 4-F | 1 |
| (CH$_2$)$_2$CH$_3$ | CH$_2$CH$_2$CH$_2$O | 4-F | 1 |
| CH$_2$CH$_3$ | CH$_2$CH$_2$OCH$_2$ | — | 0 |
| (CH$_2$)$_2$CH$_3$ | CH$_2$CH$_2$OCH$_2$ | — | 0 |
| CH$_2$CH$_3$ | CH$_2$CH$_2$OCH$_2$ | 2-F | 1 |
| (CH$_2$)$_2$CH$_3$ | CH$_2$CH$_2$OCH$_2$ | 2-F | 1 |
| CH$_2$CH$_3$ | CH$_2$CH$_2$OCH$_2$ | 3-F | 1 |
| (CH$_2$)$_2$CH$_3$ | CH$_2$CH$_2$OCH$_2$ | 3-F | 1 |
| CH$_2$CH$_3$ | CH$_2$CH$_2$OCH$_2$ | 4-F | 1 |
| (CH$_2$)$_2$CH$_3$ | CH$_2$CH$_2$OCH$_2$ | 4-F | 1 |
| CH$_2$CH$_3$ | CH$_2$CH$_2$OCH$_2$ | 4-Cl | 1 |
| (CH$_2$)$_2$CH$_3$ | CH$_2$CH$_2$OCH$_2$ | 4-Cl | 1 |
| CH$_2$CH$_3$ | CH$_2$CH$_2$OCH$_2$ | 2-CH$_3$ | 1 |
| (CH$_2$)$_2$CH$_3$ | CH$_2$CH$_2$OCH$_2$ | 2-CH$_3$ | 1 |
| CH$_2$CH$_3$ | CH$_2$CH$_2$OCH$_2$ | 3-CH$_3$ | 1 |
| (CH$_2$)$_2$CH$_3$ | CH$_2$CH$_2$OCH$_2$ | 3-CH$_3$ | 1 |
| CH$_2$CH$_3$ | CH$_2$CH$_2$OCH$_2$ | 4-CH$_3$ | 1 |
| (CH$_2$)$_2$CH$_3$ | CH$_2$CH$_2$OCH$_2$ | 4-CH$_3$ | 1 |
| CH$_2$CH$_3$ | CH$_2$CH$_2$OCH$_2$ | 4-tC$_4$H$_9$ | 1 |
| (CH$_2$)$_2$CH$_3$ | CH$_2$CH$_2$OCH$_2$ | 4-tC$_4$H$_9$ | 1 |
| CH$_2$CH$_3$ | CH$_2$CH$_2$SCH$_2$ | — | 0 |
| (CH$_2$)$_2$CH$_3$ | CH$_2$CH$_2$SCH$_2$ | — | 0 |
| CH$_2$CH$_3$ | CH$_2$CH$_2$SCH$_2$ | 4-Cl | 1 |
| (CH$_2$)$_2$CH$_3$ | CH$_2$CH$_2$SCH$_2$ | 4-Cl | 1 |
| CH$_2$CH$_3$ | CH$_2$CH$_2$SCH$_2$ | 4-F | 1 |
| (CH$_2$)$_2$CH$_3$ | CH$_2$CH$_2$SCH$_2$ | 4-F | 1 |
| CH$_2$CH$_3$ | CH$_2$CH$_2$CH$_2$CH$_2$O | — | 0 |
| (CH$_2$)$_2$CH$_3$ | CH$_2$CH$_2$CH$_2$CH$_2$O | — | 0 |
| CH$_2$CH$_3$ | CH$_2$CH$_2$CH$_2$CH$_2$O | 4-Cl | 1 |
| (CH$_2$)$_2$CH$_3$ | CH$_2$CH$_2$CH$_2$CH$_2$O | 4-Cl | 1 |
| CH$_2$CH$_3$ | CH$_2$CH$_2$CH$_2$CH$_2$O | 4-F | 1 |
| (CH$_2$)$_2$CH$_3$ | CH$_2$CH$_2$CH$_2$CH$_2$O | 4-F | 1 |
| CH$_2$CH$_3$ | CH$_2$CH$_2$CH$_2$CH$_2$CH$_2$O | — | 0 |
| (CH$_2$)$_2$CH$_3$ | CH$_2$CH$_2$CH$_2$CH$_2$CH$_2$O | — | 0 |
| CH$_2$CH$_3$ | CH$_2$CH$_2$CH$_2$CH$_2$CH$_2$O | 4-Cl | 1 |
| (CH$_2$)$_2$CH$_3$ | CH$_2$CH$_2$CH$_2$CH$_2$CH$_2$O | 4-Cl | 1 |
| CH$_2$CH$_3$ | CH$_2$CH$_2$CH$_2$CH$_2$CH$_2$O | 4-F | 1 |
| (CH$_2$)$_2$CH$_3$ | CH$_2$CH$_2$CH$_2$CH$_2$CH$_2$O | 4-F | 1 |

TABLE 26

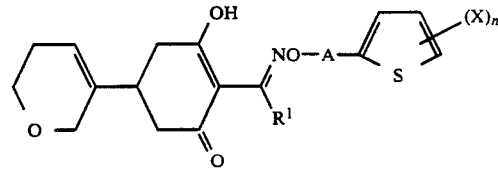

| R¹ | A | X | n |
|---|---|---|---|
| CH$_2$CH$_3$ | CH$_2$CH$_2$OCH$_2$ | — | 0 |
| (CH$_2$)$_2$CH$_3$ | CH$_2$CH$_2$OCH$_2$ | — | 0 |
| CH$_2$CH$_3$ | CH$_2$CH$_2$OCH$_2$ | 5-Cl | 1 |
| (CH$_2$)$_2$CH$_3$ | CH$_2$CH$_2$OCH$_2$ | 5-Cl | 1 |
| CH$_2$CH$_3$ | CH$_2$CH$_2$OCH$_2$ | 5-CH$_3$ | 1 |
| (CH$_2$)$_2$CH$_3$ | CH$_2$CH$_2$OCH$_2$ | 5-CH$_3$ | 1 |
| CH$_2$CH$_3$ | CH$_2$CH$_2$OCH$_2$ | 5-C$_2$H$_5$ | 1 |
| (CH$_2$)$_2$CH$_3$ | CH$_2$CH$_2$OCH$_2$ | 5-C$_2$H$_5$ | 1 |
| CH$_2$CH$_3$ | CH$_2$CH$_2$CH$_2$OCH$_2$ | — | 0 |
| (CH$_2$)$_2$CH$_3$ | CH$_2$CH$_2$CH$_2$OCH$_2$ | — | 1 |
| CH$_2$CH$_3$ | CH$_2$CH$_2$CH$_2$OCH$_2$ | 5-Cl | 1 |
| (CH$_2$)$_2$CH$_3$ | CH$_2$CH$_2$CH$_2$OCH$_2$ | 5-Cl | 1 |
| CH$_2$CH$_3$ | CH$_2$CH$_2$CH$_2$OCH$_2$ | 5-CH$_3$ | 1 |
| (CH$_2$)$_2$CH$_3$ | CH$_2$CH$_2$CH$_2$OCH$_2$ | 5-CH$_3$ | 1 |
| CH$_2$CH$_3$ | CH$_2$CH$_2$CH$_2$OCH$_2$ | 5-C$_2$H$_5$ | 1 |
| (CH$_2$)$_2$CH$_3$ | CH$_2$CH$_2$CH$_2$OCH$_2$ | 5-C$_2$H$_5$ | 1 |
| CH$_2$CH$_3$ | CH$_2$CH$_2$CH$_2$OCH$_2$CH$_2$ | — | 0 |
| (CH$_2$)$_2$CH$_3$ | CH$_2$CH$_2$CH$_2$OCH$_2$CH$_2$ | — | 0 |
| CH$_2$CH$_3$ | CH$_2$CH$_2$CH$_2$OCH$_2$CH$_2$ | 5-Cl | 1 |
| (CH$_2$)$_2$CH$_3$ | CH$_2$CH$_2$CH$_2$OCH$_2$CH$_2$ | 5-Cl | 1 |
| CH$_2$CH$_3$ | CH$_2$CH$_2$CH$_2$OCH$_2$CH$_2$ | 5-CH$_3$ | 1 |
| (CH$_2$)$_2$CH$_3$ | CH$_2$CH$_2$CH$_2$OCH$_2$CH$_2$ | 5-CH$_3$ | 1 |
| CH$_2$CH$_3$ | CH$_2$CH$_2$CH$_2$OCH$_2$CH$_2$ | 5-C$_2$H$_5$ | 1 |
| (CH$_2$)$_2$CH$_3$ | CH$_2$CH$_2$CH$_2$OCH$_2$CH$_2$ | 5-C$_2$H$_5$ | 1 |
| CH$_2$CH$_3$ | CH$_2$CH$_2$CH$_2$CH$_2$OCH$_2$ | — | 0 |
| (CH$_2$)$_2$CH$_3$ | CH$_2$CH$_2$CH$_2$CH$_2$OCH$_2$ | — | 0 |
| CH$_2$CH$_3$ | CH$_2$CH$_2$CH$_2$CH$_2$OCH$_2$ | 5-Cl | 1 |
| (CH$_2$)$_2$CH$_3$ | CH$_2$CH$_2$CH$_2$CH$_2$OCH$_2$ | 5-Cl | 1 |
| CH$_2$CH$_3$ | CH$_2$CH$_2$CH$_2$CH$_2$OCH$_2$ | 5-CH$_3$ | 1 |
| (CH$_2$)$_2$CH$_3$ | CH$_2$CH$_2$CH$_2$CH$_2$OCH$_2$ | 5-CH$_3$ | 1 |
| CH$_2$CH$_3$ | CH$_2$CH$_2$CH$_2$CH$_2$OCH$_2$ | 5-C$_2$H$_5$ | 1 |
| (CH$_2$)$_2$CH$_3$ | CH$_2$CH$_2$CH$_2$CH$_2$OCH$_2$ | 5-C$_2$H$_5$ | 1 |

TABLE 27

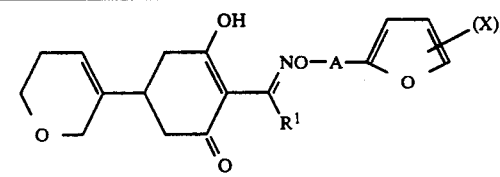

| R¹ | A | X | n |
|---|---|---|---|
| CH$_2$CH$_3$ | CH$_2$CH$_2$OCH$_2$ | — | 0 |
| (CH$_2$)$_2$CH$_3$ | CH$_2$CH$_2$OCH$_2$ | — | 0 |
| CH$_2$CH$_3$ | CH$_2$CH$_2$OCH$_2$ | 5-CH$_3$ | 1 |
| (CH$_2$)$_2$CH$_3$ | CH$_2$CH$_2$OCH$_2$ | 5-CH$_3$ | 1 |
| CH$_2$CH$_3$ | CH$_2$CH$_2$OCH$_2$ | 5-C$_2$H$_5$ | 1 |
| (CH$_2$)$_2$CH$_3$ | CH$_2$CH$_2$OCH$_2$ | 5-C$_2$H$_5$ | 1 |
| CH$_2$CH$_3$ | CH$_2$CH$_2$CH$_2$OCH$_2$ | — | 0 |
| (CH$_2$)$_2$CH$_3$ | CH$_2$CH$_2$CH$_2$OCH$_2$ | — | 0 |
| CH$_2$CH$_3$ | CH$_2$CH$_2$CH$_2$OCH$_2$ | 5-CH$_3$ | 1 |
| (CH$_2$)$_2$CH$_3$ | CH$_2$CH$_2$CH$_2$OCH$_2$ | 5-CH$_3$ | 1 |
| CH$_2$CH$_3$ | CH$_2$CH$_2$CH$_2$OCH$_2$ | 5-C$_2$H$_5$ | 1 |
| (CH$_2$)$_2$CH$_3$ | CH$_2$CH$_2$CH$_2$OCH$_2$ | 5-C$_2$H$_5$ | 1 |
| CH$_2$CH$_3$ | CH$_2$CH$_2$CH$_2$OCH$_2$CH$_2$ | — | 0 |
| (CH$_2$)$_2$CH$_3$ | CH$_2$CH$_2$CH$_2$OCH$_2$CH$_2$ | — | 0 |
| CH$_2$CH$_3$ | CH$_2$CH$_2$CH$_2$OCH$_2$CH$_2$ | 5-CH$_3$ | 1 |
| (CH$_2$)$_2$CH$_3$ | CH$_2$CH$_2$CH$_2$OCH$_2$CH$_2$ | 5-CH$_3$ | 1 |
| CH$_2$CH$_3$ | CH$_2$CH$_2$CH$_2$OCH$_2$CH$_2$ | 5-C$_2$H$_5$ | 1 |
| (CH$_2$)$_2$CH$_3$ | CH$_2$CH$_2$CH$_2$OCH$_2$CH$_2$ | 5-C$_2$H$_5$ | 1 |
| CH$_2$CH$_3$ | CH$_2$CH$_2$CH$_2$CH$_2$OCH$_2$ | — | 0 |
| (CH$_2$)$_2$CH$_3$ | CH$_2$CH$_2$CH$_2$CH$_2$OCH$_2$ | — | 0 |
| CH$_2$CH$_3$ | CH$_2$CH$_2$CH$_2$CH$_2$OCH$_2$ | 5-CH$_3$ | 1 |
| (CH$_2$)$_2$CH$_3$ | CH$_2$CH$_2$CH$_2$CH$_2$OCH$_2$ | 5-CH$_3$ | 1 |
| CH$_2$CH$_3$ | CH$_2$CH$_2$CH$_2$CH$_2$OCH$_2$ | 5-C$_2$H$_5$ | 1 |

TABLE 27-continued

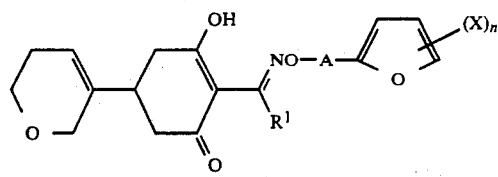

| R¹ | A | X | n |
|---|---|---|---|
| (CH₂)₂CH₃ | CH₂CH₂CH₂CH₂OCH₂ | 5-C₂H₅ | 1 |

TABLE 28

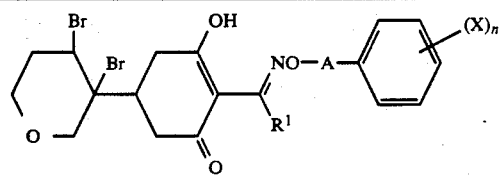

| R¹ | A | X | n |
|---|---|---|---|
| CH₂CH₃ | CH₂CH₂O | — | 0 |
| (CH₂)₂CH₃ | CH₂CH₂O | — | 0 |
| CH₂CH₃ | CH₂CH₂O | 2-Cl | 1 |
| (CH₂)₂CH₃ | CH₂CH₂O | 2-Cl | 1 |
| CH₂CH₃ | CH₂CH₂O | 3-Cl | 1 |
| (CH₂)₂CH₃ | CH₂CH₂O | 3-Cl | 1 |
| CH₂CH₃ | CH₂CH₂O | 4-Cl | 1 |
| (CH₂)₂CH₃ | CH₂CH₂O | 4-Cl | 1 |
| CH₂CH₃ | CH₂CH₂O | 2-F | 1 |
| (CH₂)₂CH₃ | CH₂CH₂O | 2-F | 1 |
| CH₂CH₃ | CH₂CH₂O | 3-F | 1 |
| (CH₂)₂CH₃ | CH₂CH₂O | 3-F | 1 |
| CH₂CH₃ | CH₂CH₂O | 4-F | 1 |
| (CH₂)₂CH₃ | CH₂CH₂O | 4-F | 1 |
| CH₂CH₃ | CH₂CH₂O | 3-CF₃ | 1 |
| (CH₂)₂CH₃ | CH₂CH₂O | 3-CF₃ | 1 |
| CH₂CH₃ | CH₂CH₂CH₂O | — | 0 |
| (CH₂)₂CH₃ | CH₂CH₂CH₂O | — | 0 |
| CH₂CH₃ | CH₂CH₂CH₂O | 4-Cl | 1 |
| (CH₂)₂CH₃ | CH₂CH₂CH₂O | 4-Cl | 1 |
| CH₂CH₃ | CH₂CH₂CH₂O | 4-F | 1 |
| (CH₂)₂CH₃ | CH₂CH₂CH₂O | 4-F | 1 |
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 2-F | 1 |
| (CH₂)₂CH₃ | CH₂CH₂OCH₂ | 2-F | 1 |
| CH₂CH₃ | CH₂CH₂OCH₂ | 3-F | 1 |
| (CH₂)₂CH₃ | CH₂CH₂OCH₂ | 3-F | 1 |
| CH₂CH₃ | CH₂CH₂OCH₂ | 4-F | 1 |
| (CH₂)₂CH₃ | CH₂CH₂OCH₂ | 4-F | 1 |
| CH₂CH₃ | CH₂CH₂OCH₂ | 4-Cl | 1 |
| (CH₂)₂CH₃ | CH₂CH₂OCH₂ | 4-Cl | 1 |
| CH₂CH₃ | CH₂CH₂OCH₂ | 2-CH₃ | 1 |
| (CH₂)₂CH₃ | CH₂CH₂OCH₂ | 2-CH₃ | 1 |
| CH₂CH₃ | CH₂CH₂OCH₂ | 3-CH₃ | 1 |
| (CH₂)₂CH₂ | CH₂CH₂OCH₂ | 3-CH₃ | 1 |
| CH₂CH₃ | CH₂CH₂OCH₂ | 4-CH₃ | 1 |
| (CH₂)₂CH₃ | CH₂CH₂OCH₂ | 4-CH₃ | 1 |
| CH₂CH₃ | CH₂CH₂OCH₂ | 4-tC₄H₉ | 1 |
| (CH₂)₂CH₃ | CH₂CH₂OCH₂ | 4-tC₄H₉ | 1 |
| CH₂CH₃ | CH₂CH₂SCH₂ | — | 0 |
| (CH₂)₂CH₃ | CH₂CH₂SCH₂ | — | 0 |
| CH₂CH₃ | CH₂CH₂SCH₂ | 4-Cl | 1 |
| (CH₂)₂CH₃ | CH₂CH₂SCH₂ | 4-Cl | 1 |
| CH₂CH₃ | CH₂CH₂SCH₂ | 4-F | 1 |
| (CH₂)₂CH₃ | CH₂CH₂SCH₂ | 4-F | 1 |
| CH₂CH₃ | CH₂CH₂CH₂CH₂O | — | 0 |
| (CH₂)₂CH₃ | CH₂CH₂CH₂CH₂O | — | 0 |
| CH₂CH₃ | CH₂CH₂CH₂CH₂O | 4-Cl | 1 |
| (CH₂)₂CH₃ | CH₂CH₂CH₂CH₂O | 4-Cl | 1 |
| CH₂CH₃ | CH₂CH₂CH₂CH₂O | 4-F | 1 |
| (CH₂)₂CH₃ | CH₂CH₂CH₂CH₂O | 4-F | 1 |
| CH₂CH₃ | CH₂CH₂CH₂CH₂CH₂O | — | 0 |
| (CH₂)₂CH₃ | CH₂CH₂CH₂CH₂CH₂O | — | 0 |
| CH₂CH₃ | CH₂CH₂CH₂CH₂CH₂O | 4-Cl | 1 |
| (CH₂)₂CH₃ | CH₂CH₂CH₂CH₂CH₂O | 4-Cl | 1 |

TABLE 28-continued

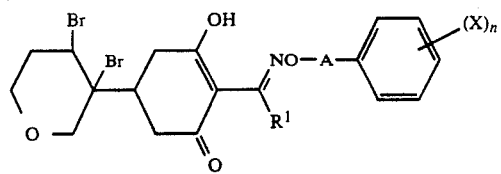

| R¹ | A | X | n |
|---|---|---|---|
| CH₂CH₃ | CH₂CH₂CH₂CH₂CH₂O | 4-F | 1 |
| (CH₂)₂CH₃ | CH₂CH₂CH₂CH₂CH₂O | 4-F | 1 |

TABLE 29

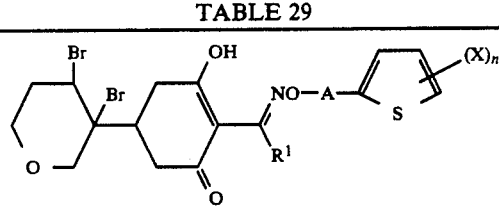

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-Cl | 1 |
| (CH₂)₂CH₃ | CH₂CH₂OCH₂ | 5-Cl | 1 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |
| CH₂CH₃ | CH₂CH₂CH₂OCH₂ | 5-Cl | 1 |
| (CH₂)₂CH₃ | CH₂CH₂CH₂OCH₂ | 5-Cl | 1 |
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₂ | CH₂CH₂CH₂OCH₂CH₂ | — | 0 |
| CH₂CH₃ | CH₂CH₂CH₂OCH₂CH₂ | 5-Cl | 1 |
| (CH₂)₂CH₃ | CH₂CH₂CH₂OCH₂CH₂ | 5-Cl | 1 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-Cl | 1 |
| (CH₂)₂CH₃ | CH₂CH₂CH₂CH₂OCH₂ | 5-Cl | 1 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

TABLE 30

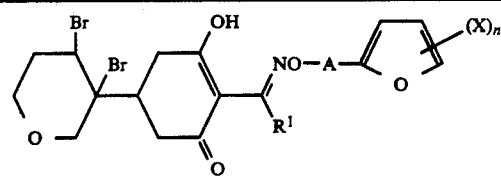

| R¹ | A | X | n |
|---|---|---|---|
| CH₂CH₃ | CH₂CH₂OCH₂ | — | 0 |
| (CH₂)₂CH₃ | CH₂CH₂OCH₂ | — | 0 |
| CH₂CH₃ | CH₂CH₂OCH₂ | 5-CH₃ | 1 |
| (CH₂)₂CH₃ | CH₂CH₂OCH₂ | 5-CH₃ | 1 |
| CH₂CH₃ | CH₂CH₂OCH₂ | 5-C₂H₅ | 1 |
| (CH₂)₂CH₃ | CH₂CH₂OCH₂ | 5-C₂H₅ | 1 |
| CH₂CH₃ | CH₂CH₂CH₂OCH₂ | — | 0 |
| (CH₂)₂CH₃ | CH₂CH₂CH₂OCH₂ | — | 0 |

TABLE 30-continued

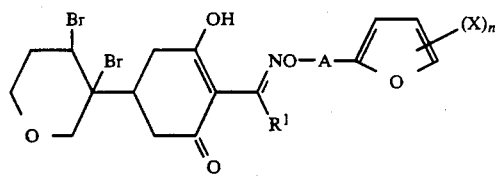

| R¹ | A | X | n |
|---|---|---|---|
| CH₂CH₃ | CH₂CH₂CH₂OCH₂ | 5-CH₃ | 1 |
| (CH₂)₂CH₃ | CH₂CH₂CH₂OCH₂ | 5-CH₃ | 1 |
| CH₂CH₃ | CH₂CH₂CH₂OCH₂ | 5-C₂H₅ | 1 |
| (CH₂)₂CH₃ | CH₂CH₂CH₂OCH₂ | 5-C₂H₅ | 1 |
| CH₂CH₃ | CH₂CH₂CH₂OCH₂CH₂ | — | 0 |
| (CH₂)₂CH₃ | CH₂CH₂CH₂OCH₂CH₂ | — | 0 |
| CH₂CH₃ | CH₂CH₂CH₂OCH₂CH₂ | 5-CH₃ | 1 |
| (CH₂)₂CH₃ | CH₂CH₂CH₂OCH₂CH₂ | 5-CH₃ | 1 |
| CH₂CH₃ | CH₂CH₂CH₂OCH₂CH₂ | 5-C₂H₅ | 1 |
| (CH₂)₂CH₃ | CH₂CH₂CH₂OCH₂CH₂ | 5-C₂H₅ | 1 |
| CH₂CH₃ | CH₂CH₂CH₂CH₂OCH₂ | — | 0 |
| (CH₂)₂CH₃ | CH₂CH₂CH₂CH₂OCH₂ | — | 0 |
| CH₂CH₃ | CH₂CH₂CH₂CH₂OCH₂ | 5-CH₃ | 1 |
| (CH₂)₂CH₃ | CH₂CH₂CH₂CH₂OCH₂ | 5-CH₃ | 1 |
| CH₂CH₃ | CH₂CH₂CH₂CH₂OCH₂ | 5-C₂H₅ | 1 |
| (CH₂)₂CH₃ | CH₂CH₂CH₂CH₂OCH₂ | 5-C₂H₅ | 1 |

Cyclohexenone oxime ethers where Z is phenyl are particularly preferred. The cyclohexenone oxime ethers are suitable as herbicides, particularly for combating plants from the Gramineae family (grasses).

The cyclohexenone derivatives I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possible solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.5 to 90, % by weight of active ingredient. The active ingredients are used in a purity of from 90 to 100, and preferably from 95 to 100, % (according to GC/HPLC or the NMR spectrum).

Examples of formulations are as follows:

I. 90 parts by weight of compound no. 7.21 is mixed with 10 parts by weight of N-methyl-alpha-pyrrolidone. A mixture is obtained which is suitable for application in the form of very fine drops.

II. 20 parts by weight of compound no. 7.23 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 7.21 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 7.23 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 7.23 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 7.15 is intimately mixed with 97 parts by weight of particulate kaolin. A dust is obtained containing 3% by weight of the active ingredient.

VII. 30 parts by weight of compound no. 7.21 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 7.23 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the time of the year, the plants to be combated and their growth stage, and vary from 0.001 to 3, and are preferably from 0.01 to 2.0, kg/ha.

In view of the spectrum of weeds which can be combated, the tolerance of the active ingredients by crop plants, the desired influence on growth, and in view of the numerous application methods possible, the compounds according to the invention may be used in a large number of crops. Those which follow are given by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn |

To increase the spectrum of action and to achieve synergistic effects, the cyclohexenone derivatives I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the cyclohexenone derivatives I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

The directions given in the synthesis examples below were employed, after appropriate modification of the starting materials, to obtain further hydroxylamines of the formula III and cyclohexenone oxime ethers of the formula I; the compounds obtained are listed with their physical details in the tables which follow.

EXAMPLE ILLUSTRATING THE SYNTHESIS OF THE HYDROXYLAMINES III

N-[2-(2-Fluorobenzyloxy)-ethoxy]-phthalimide

At 20° to 25° C. and over a period of 1 hour, 108 ml of triethylamine was dripped into a mixture of 165 g (0.71 mol) of 1-bromo-2-(2-fluorobenzyloxy)-ethane, 116 g (0.7 mol) of N-hydroxyphthalimide and 710 ml of N-methyl-2-pyrrolidone. After the mixture had been kept for 5 hours at 60° C., the cold mixture was poured into 2000 ml of ice water, the precipitate was suction filtered, washed with water and isopropanol and dried under reduced pressure over phosphorus pentoxide. There was obtained 185 g (82%) of phthalimide ether, m.p. 62°-64° C. $^1$H-NMR (250 MHZ, $d_6$-DMSO): $\delta = 3.85$ (m,2H), 4.35 (m,2H), 4.54 (s,2H), 7.10–7.40 (m,4H), 7.88 (s,4H).

O-[2-(2-Fluorobenzyloxy)-ethyl]-hydroxylamine 184 g (0.58 mol) of the phthalimide ether prepared above was added in portions to 270 ml of ethanolamine. After the mixture had been kept for 3 hours at 60° C., the cold mixture was poured into 1000 ml of ice water. The hydrolysate was extracted three times, each time with 800 ml of dichloromethane. The combined organic phases were washed with 200 ml of saturated sodium chloride solution, dried over magnesium sulfate and evaporated down under reduced pressure. There was obtained 98 g (91%) of the hydroxylamine. $^1$H-NMR (250 MHZ, CDCl$_3$): $\delta = 3.70$ (dd,2H), 3.85 (dd,2H), 4.54 (s,2H), 5.50 (bs,2H), 7.00–7.50 (m,4H).

EXAMPLE ILLUSTRATING THE SYNTHESIS OF CYCLOHEXENONE OXIME ETHERS I

2-[1-[[2-(2-Fluorobenzyloxy)ethoxy]imino]butyl]-3-hydroxy-5-(2H-tetrahydropyran-4-yl)-2-cyclohexen-1-one A mixture of 4.0 g (10 mmol) of 2-butyryl-3-hydroxy-5-(2H-tetrahydropyran-4-yl)-2-cyclohexen-1-one and 2.6 g (14 mmol) of O-[2-(2-fluorobenzyloxy)ethyl]hydroxylamine in 100 ml of methanol was stirred for 24 hours. It was then evaporated down under reduced pressure, and the crude product was chromatographed using 100 g of silica gel/column 30×4 cm (developer: ether). There was obtained 3.5 g (54%) of the cyclohexenone oxime ether. $^1$H-NMR (300 MHZ, CDCl$_3$): $\delta = 0.93$ (t,3H), 1.20–1.77 (m,7H), 1.90 (m,1H), 2.23 (m,2H), 2.58 (m,2H), 2.92 (m,2H), 3.38 (t,2H), 3.80 (m,2H), 4.03 (m,2H), 4.25 (m,2H), 4.68 (s,2H), 6.93–7.50 (m,4H), 14.30 (s,1H).

TABLE A $H_2N-O-A-Z-X_n$     III

| No. | A | Z | X | n | Phys. data/NMR data in ppm |
|---|---|---|---|---|---|
| 1.01 | CH$_2$CH$_2$O | Phenyl | — | 0 | 6.90(m, 3H), 7.27(m, 2H) |
| 1.02 | CH$_2$CH$_2$O | Phenyl | 2-F | 1 | 6.85–7.15(m, 4H) |
| 1.03 | CH$_2$CH$_2$O | Phenyl | 3-F | 1 | 6.70(m, 3H), 7, 25(m, 1H) |
| 1.04 | CH$_2$CH$_2$O | Phenyl | 4-F | 1 | 6.80–7.00(m, 4H) |
| 1.05 | CH$_2$CH$_2$O | Phenyl | 2-Cl | 1 | |
| 1.06 | CH$_2$CH$_2$O | Phenyl | 3-Cl | 1 | |
| 1.07 | CH$_2$CH$_2$O | Phenyl | 4-Cl | 1 | 6.85(m, 2H), 7.25(m, 2H) |
| 1.08 | CH$_2$CH$_2$O | Phenyl | 2-CF$_3$ | 1 | |
| 1.09 | CH$_2$CH$_2$O | Phenyl | 3-CF$_3$ | 1 | |
| 1.10 | CH$_2$CH$_2$O | Phenyl | 4-CF$_3$ | 1 | |
| 1.11 | CH$_2$CH$_2$O | Phenyl | 2,4-Cl$_2$ | 2 | 6.83(d, 1H), 7.15(dd, 1H), 7.85(d, 1H) |
| 1.12 | CH$_2$CH$_2$O | Phenyl | 2,4,6-Cl$_3$ | 3 | 7.30(s, 2H) |
| 1.13 | CH$_2$CH$_2$O | Phenyl | 4-NO$_2$ | 1 | 7.00(d, 2H), 8.20(d, 2H) |
| 1.14 | CH$_2$CH(CH$_3$)O | Phenyl | — | 0 | |
| 1.15 | CH$_2$CH(CH$_3$)O | Phenyl | 4-F | 1 | |
| 1.16 | CH$_2$CH(CH$_3$)O | Phenyl | 4-Cl | 1 | |
| 1.17 | CH$_2$CH$_2$S | Phenyl | — | 0 | 7.17–7.43(m, 5H) |
| 1.18 | CH$_2$CH$_2$S | Phenyl | 4-F | 1 | 7.00(m, 2H), 7.40(m, 2H) |
| 1.19 | CH$_2$CH$_2$S | Phenyl | 2-Cl | 1 | 7.06–7.40(m, 4H) |
| 1.20 | CH$_2$CH$_2$S | Phenyl | 4-Cl | 1 | 7.30(m, 4H) |
| 1.21 | CH$_2$CH$_2$S | Phenyl | 2,6-Cl$_2$ | 2 | 7.15(t, 1H), 7.33(d, 2H) |
| 1.22 | CH$_2$CH$_2$CH$_2$O | Phenyl | — | 0 | 6.90(m, 3H), 7.27(m, 2H) |
| 1.23 | CH$_2$CH$_2$CH$_2$O | Phenyl | 2-F | 1 | 6.80–7.15(m, 4H) |
| 1.24 | CH$_2$CH$_2$CH$_2$O | Phenyl | 3-F | 1 | 6.70(m, 3H), 7.25(m, 1H) |
| 1.25 | CH$_2$CH$_2$CH$_2$O | Phenyl | 4-F | 1 | 6.80–7.00(m, 4H) |
| 1.26 | CH$_2$CH$_2$CH$_2$O | Phenyl | 2-Cl | 1 | 6.80–7.00(m, 2H), 7.20(m, 1H), 7.35(m, 1H) |
| 1.27 | CH$_2$CH$_2$CH$_2$O | Phenyl | 3-Cl | 1 | 6.80(m, 1H), 6.95(m, 2H), 7.20(m, 1H) |
| 1.28 | CH$_2$CH$_2$CH$_2$O | Phenyl | 4-Cl | 1 | 6.80(m, 2H), 7.20(m, 2H) |
| 1.29 | CH$_2$CH$_2$CH$_2$O | Phenyl | 4-NO$_2$ | 1 | 7.00(d, 2H), 8.15(d, 2H) |
| 1.30 | CH$_2$CH$_2$CH$_2$S | Phenyl | — | 0 | 7.15–7.40(m, 5H) |
| 1.31 | CH$_2$CH$_2$CH$_2$S | Phenyl | 4-F | 1 | 7.00(m, 2H), 7.40(m, 2H) |
| 1.32 | CH$_2$CH$_2$CH$_2$S | Phenyl | 2-Cl | 1 | 7.07–7.40(m, 4H) |
| 1.33 | CH$_2$CH$_2$CH$_2$S | Phenyl | 3-Cl | 1 | 7.17(m, 3H), 7.30(m, 1H) |
| 1.34 | CH$_2$CH$_2$CH$_2$S | Phenyl | 4-Cl | 1 | 7.25(m, 4H) |
| 1.35 | CH$_2$CH$_2$CH$_2$S | Phenyl | 2,5-Cl$_2$ | 2 | 7.03(dd, 1H), 7.20(d, 1H), 7.23(d, 1H) |

TABLE A-continued $$H_2N-O-A-Z-X_n \quad\quad III$$

| No. | A | Z | X | n | Phys. data/NMR data in ppm |
|---|---|---|---|---|---|
| 1.36 | $CH_2CH_2CH_2S$ | Phenyl | 2,6-$Cl_2$ | 2 | 7.15(t, 1H), 7.33(d, 2H) |
| 1.37 | $CH_2CH_2OCH_2$ | Phenyl | — | 0 | 7.25(m, 5H) |
| 1.38 | $CH_2CH_2OCH_2$ | Phenyl | 2-F | 1 | 3.70(dd, 2H), 3.85(dd, 2H), 4.54(s, 2H), 5.50(bs, 2H), 7.00–7.50(m, 4H) |
| 1.39 | $CH_2CH_2OCH_2$ | Phenyl | 3-F | 1 | |
| 1.40 | $CH_2CH_2OCH_2$ | Phenyl | 4-F | 1 | 3.66(dd, 2H), 3.88(dd, 2H), 4.54(s, 2H), 5.50(bs, 2H), 7.00–7.10(m, 2H), 7.20–7.40(m, 2H) |
| 1.41 | $CH_2CH_2OCH_2$ | Phenyl | 2-Cl | 1 | |
| 1.42 | $CH_2CH_2OCH_2$ | Phenyl | 3-Cl | 1 | |
| 1.43 | $CH_2CH_2OCH_2$ | Phenyl | 4-Cl | 1 | 3.65(dd, 2H), 3.84(dd, 2H), 4.54(s, 2H), 5.50(bs, 2H), 7.20–7.40(m, 4H) |
| 1.44 | $CH_2CH_2OCH_2$ | Phenyl | 2-$CH_3$ | 1 | |
| 1.45 | $CH_2CH_2OCH_2$ | Phenyl | 3-$CH_3$ | 1 | 2.35(s, 3H), 3.65(dd, 2H), 3.87(dd, 2H), 4.54(s, 2H), 5.50(bs, 2H), 7.00–7.30(m, 4H) |
| 1.46 | $CH_2CH_2OCH_2$ | Phenyl | 4-$CH_3$ | 1 | 2.35(s, 3H), 3.64(dd, 2H), 3.84(dd, 2H), 4.53(s, 2H), 5.50(bs, 2H), 7.10–7.30(m, 4H) |
| 1.47 | $CH_2CH_2OCH_2$ | Phenyl | 4-$tC_4H_9$ | 1 | 1.33(s, 9H), 3.65(dd, 2H), 3.89(dd, 2H), 4.55(s, 2H), 5.50(bs, 2H), 7.20–7.50(m, 4H) |
| 1.48 | $CH_2CH_2SCH_2$ | Phenyl | — | 0 | 2.66(t, 2H), 3.70–3.85(m, 4H), 5.40(bs, 2H), 7.20–7.50(m, 5H) |
| 1.49 | $CH_2CH_2SCH_2$ | Phenyl | 4-F | 1 | 7.00(m, 2H), 7.25(m, 2H) |
| 1.50 | $CH_2CH_2SCH_2$ | Phenyl | 4-Cl | 1 | 2.65(t, 2H), 3.72(s, 2H), 3.78(t, 2H), 5.40(bs, 2H), 7.28(s, 4H) |
| 1.51 | $CH_2CH_2CH_2CH_2O$ | Phenyl | — | 0 | |
| 1.52 | $CH_2CH_2CH_2CH_2O$ | Phenyl | 2-F | 1 | |
| 1.53 | $CH_2CH_2CH_2CH_2O$ | Phenyl | 3-F | 1 | |
| 1.54 | $CH_2CH_2CH_2CH_2O$ | Phenyl | 4-F | 1 | 6.80–7.00(m, 4H) |
| 1.55 | $CH_2CH_2CH_2CH_2O$ | Phenyl | 4-Cl | 1 | 6.80(m, 2H), 7.20(m, 2H) |
| 1.56 | $CH_2CH_2CH_2CH_2O$ | Phenyl | 2,6-$Cl_2$ | 2 | 6.95(t, 1H), 7.30(d, 2H) |
| 1.57 | $CH_2CH_2OCH_2CH_2$ | Phenyl | — | 0 | |
| 1.58 | $CH_2CH_2OCH_2CH_2$ | Phenyl | 4-F | 1 | 6.93(m, 2H), 7.13(m, 2H) |
| 1.59 | $CH_2CH_2OCH_2CH_2$ | Phenyl | 4-Cl | 1 | |
| 1.60 | $CH_2CH_2CH_2CH_2CH_2O$ | Phenyl | — | 0 | |
| 1.61 | $CH_2CH_2CH_2CH_2CH_2O$ | Phenyl | 4-F | 1 | |
| 1.62 | $CH_2CH_2CH_2CH_2CH_2O$ | Phenyl | 4-Cl | 1 | |

TABLE B

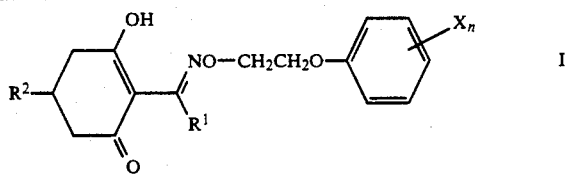

$$(A = -CH_2CH_2O-; \; Z = Phenyl) \quad I$$

| No. | $R^1$ | $R^2$ | $X_n$ | Phys. data/NMR data in ppm, mp in °C. |
|---|---|---|---|---|
| 2.01 | Ethyl | Tetrahydropyran-3-yl | — | 42–45 |
| 2.02 | Propyl | Tetrahydropyran-3-yl | — | 3.90(m, 2H), 4.20(t, 2H), 4.40(m, 2H) 6.80–7.00(m, 3H), 7.13–7.37(m, 2H), |
| 2.03 | Ethyl | Tetrahydropyran-4-yl | — | 106–107 |
| 2.04 | Propyl | Tetrahydropyran-4-yl | — | 72–73 |
| 2.05 | Ethyl | Tetrahydrothiopyran-3-yl | — | 52–55 |
| 2.06 | Propyl | Tetrahydrothiopyran-3-yl | — | 92 |
| 2.07 | Ethyl | Tetrahydropyran-3-yl | 2-F | 76–78 |
| 2.08 | Propyl | Tetrahydropyran-3-yl | 2-F | 72–77 |
| 2.09 | Ethyl | Tetrahydropyran-4-yl | 2-F | 121–125 |
| 2.10 | Propyl | Tetrahydropyran-4-yl | 2-F | 103–107 |
| 2.11 | Ethyl | Tetrahydrothiopyran-3-yl | 2-F | 82–86 |
| 2.12 | Propyl | Tetrahydrothiopyran-3-yl | 2-F | 81–85 |
| 2.13 | Ethyl | Tetrahydropyran-3-yl | 3-F | 62–68 |
| 2.14 | Propyl | Tetrahydropyran-3-yl | 3-F | 3.90(m, 2H), 4.20(t, 2H), 4.40(m, 2H) 6.70(m, 3H), 7.25(m, 1H), |
| 2.15 | Ethyl | Tetrahydropyran-4-yl | 3-F | 103–109 |
| 2.16 | Propyl | Tetrahydropyran-4-yl | 3-F | 73–79 |
| 2.17 | Ethyl | Tetrahydrothiopyran-3-yl | 3-F | 4.20(t, 2H), 4.40(m, 2H) 6.70(m, 3H), 7.25(m, 1H) |
| 2.18 | Propyl | Tetrahydrothiopyran-3-yl | 3-F | |
| 2.19 | Ethyl | Tetrahydropyran-3-yl | 4-F | 64–67 |
| 2.20 | Propyl | Tetrahydropyran-3-yl | 4-F | 70–72 |
| 2.21 | Ethyl | Tetrahydropyran-4-yl | 4-F | 101–103 |
| 2.22 | Propyl | Tetrahydropyran-4-yl | 4-F | 107–109 |
| 2.23 | Ethyl | Tetrahydrothiopyran-3-yl | 4-F | 105–108 |
| 2.24 | Propyl | Tetrahydrothiopyran-3-yl | 4-F | 82–84 |
| 2.25 | Ethyl | Tetrahydropyran-3-yl | 2-Cl | 74–80 |
| 2.26 | Propyl | Tetrahydropyran-3-yl | 2-Cl | 67–71 |

TABLE B-continued

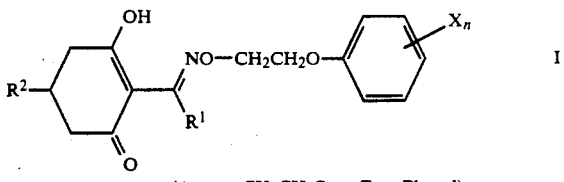

(A = —CH₂CH₂O—; Z = Phenyl)

| No. | R¹ | R² | Xₙ | Phys. data/NMR data in ppm, mp in °C. |
|---|---|---|---|---|
| 2.27 | Ethyl | Tetrahydropyran-4-yl | 2-Cl | 4.00(m, 2H), 4.27(t, 2H), 4.47(m, 2H), 7.20(t, 1H), 7.37(d, 1H) |
| 2.28 | Propyl | Tetrahydropyran-4-yl | 2-Cl | 68–72 |
| 2.29 | Ethyl | Tetrahydrothiopyran-3-yl | 2-Cl | 74–78 |
| 2.30 | Propyl | Tetrahydrothiopyran-3-yl | 2-Cl | 72–78 |
| 2.31 | Ethyl | Tetrahydropyran-3-yl | 3-Cl | |
| 2.32 | Propyl | Tetrahydropyran-3-yl | 3-Cl | |
| 2.33 | Ethyl | Tetrahydropyran-4-yl | 3-Cl | |
| 2.34 | Propyl | Tetrahydropyran-4-yl | 3-Cl | |
| 2.35 | Ethyl | Tetrahydrothiopyran-3-yl | 3-Cl | |
| 2.36 | Propyl | Tetrahydrothiopyran-3-yl | 3-Cl | |
| 2.37 | Ethyl | Tetrahydropyran-3-yl | 4-Cl | 3.93(m, 2H), 4.20(t, 2H), 4.43(m, 2H), 6.90(m, 2H), 7.25(m, 2H) |
| 2.38 | Propyl | Tetrahydropyran-3-yl | 4-Cl | 3.93(m, 2H), 4.20(t, 2H), 4.43(m, 2H), 6.90(m, 2H), 7.25(m, 2H) |
| 2.39 | Ethyl | Tetrahydropyran-4-yl | 4-Cl | 116–118 |
| 2.40 | Propyl | Tetrahydropyran-4-yl | 4-Cl | 104–106 |
| 2.41 | Ethyl | Tetrahydrothiopyran-3-yl | 4-Cl | 74–77 |
| 2.42 | Propyl | Tetrahydrothiopyran-3-yl | 4-Cl | 86–88 |
| 2.43 | Ethyl | Tetrahydropyran-3-yl | 2-CF₃ | |
| 2.44 | Propyl | Tetrahydropyran-3-yl | 2-CF₃ | |
| 2.45 | Ethyl | Tetrahydropyran-4-yl | 2-CF₃ | |
| 2.46 | Propyl | Tetrahydropyran-4-yl | 2-CF₃ | |
| 2.47 | Ethyl | Tetrahydrothiopyran-3-yl | 2-CF₃ | |
| 2.48 | Propyl | Tetrahydrothiopyran-3-yl | 2-CF₃ | |
| 2.49 | Ethyl | Tetrahydropyran-3-yl | 3-CF₃ | |
| 2.50 | Propyl | Tetrahydropyran-3-yl | 3-CF₃ | |
| 2.51 | Ethyl | Tetrahydropyran-4-yl | 3-CF₃ | |
| 2.52 | Propyl | Tetrahydropyran-4-yl | 3-CF₃ | |
| 2.53 | Ethyl | Tetrahydrothiopyran-3-yl | 3-CF₃ | |
| 2.54 | Propyl | Tetrahydrothiopyran-3-yl | 3-CF₃ | |
| 2.55 | Ethyl | Tetrahydropyran-3-yl | 4-CF₃ | 72–77 |
| 2.56 | Propyl | Tetrahydropyran-3-yl | 4-CF₃ | 3.90(m, 2H), 4.27(t, 2H), 4.47(m, 2H) 7.00(d, 2H), 7.55(d, 2H) |
| 2.57 | Ethyl | Tetrahydropyran-4-yl | 4-CF₃ | |
| 2.58 | Propyl | Tetrahydropyran-4-yl | 4-CF₃ | 90–94 |
| 2.59 | Ethyl | Tetrahydrothiopyran-3-yl | 4-CF₃ | 73–79 |
| 2.60 | Propyl | Tetrahydrothiopyran-3-yl | 4-CF₃ | 4.27(t, 2H), 4.47(m, 2H), 7.00(d, 2H) 7.55(d, 2H) |
| 2.61 | Ethyl | Tetrahydropyran-3-yl | 2,4-Cl₂ | 73–75 |
| 2.62 | Propyl | Tetrahydropyran-3-yl | 2,4-Cl₂ | 69–73 |
| 2.63 | Ethyl | Tetrahydropyran-4-yl | 2,4-Cl₂ | 4.00(m, 2H), 4.25(t, 2H), 4.45(t, 2H) 6.87(d, 1H), 7.17(d, 1H), 7.37(d, 1H) |
| 2.64 | Propyl | Tetrahydropyran-4-yl | 2,4-Cl₂ | 4.00(m, 2H), 4.25(t, 2H), 4.45(t, 2H) 6.87(d, 1H), 7.17(d, 1H), 7.37(d, 1H) |
| 2.65 | Ethyl | Tetrahydrothiopyran-3-yl | 2,4-Cl₂ | 4.25(t, 2H), 4.45(t, 2H), 6.87(d, 1H) 7.17(d, 1H), 7.37(d, 1H) |
| 2.66 | Propyl | Tetrahydrothiopyran-3-yl | 2,4-Cl₂ | 4.25(t, 2H), 4.45(t, 2H), 6.87(d, 1H) 7.17(d, 1H), 7.37(d, 1H) |
| 2.67 | Ethyl | Tetrahydropyran-3-yl | 2,4,6-Cl₃ | 90–93 |
| 2.68 | Propyl | Tetrahydropyran-3-yl | 2,4,6-Cl₃ | 83–87 |
| 2.69 | Ethyl | Tetrahydropyran-4-yl | 2,4,6-Cl₃ | 79–82 |
| 2.70 | Propyl | Tetrahydropyran-4-yl | 2,4,6-Cl₃ | 4.00(m, 2H), 4.27(t, 2H), 4.45(m, 2H), 7.32(s, 2H) |
| 2.71 | Ethyl | Tetrahydrothiopyran-3-yl | 2,4,6-Cl₃ | 105–108 |
| 2.72 | Propyl | Tetrahydrothiopyran-3-yl | 2,4,6-Cl₃ | 4.27(t, 2H), 4.45(m, 2H), 7.82(s, 2H) |
| 2.73 | Ethyl | Tetrahydropyran-3-yl | 4-NO₂ | 3.90(m, 2H), 4.32(m, 2H), 4.50(m, 2H), 7.00(d, 2H), 8.20(d, 2H) |
| 2.74 | Propyl | Tetrahydropyran-3-yl | 4-NO₂ | 3.90(m, 2H), 4.32(m, 2H), 4.50(m, 2H) 7.00(d, 2H), 8.20(d, 2H) |
| 2.75 | Ethyl | Tetrahydropyran-4-yl | 4-NO₂ | 126–129 |
| 2.76 | Propyl | Tetrahydropyran-4-yl | 4-NO₂ | 138–141 |
| 2.77 | Ethyl | Tetrahydrothiopyran-3-yl | 4-NO₂ | 4.32(m, 2H), 4.50(m, 2H), 7.00(d, 2H), 8.20(d, 2H) |
| 2.78 | Propyl | Tetrahydrothiopyran-3-yl | 4-NO₂ | 4.32(m, 2H), 4.50(m, 2H), 7.00(d, 2H) 8.20(d, 2H) |

TABLE C

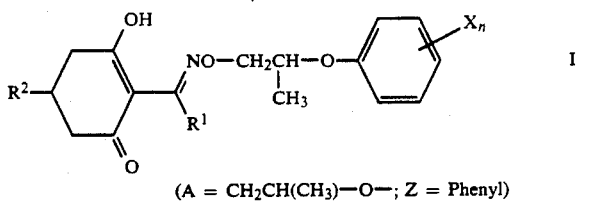

(A = CH$_2$CH(CH$_3$)—O—; Z = Phenyl)

| No. | R$^1$ | R$^2$ | X$_n$ | Phys. data/NMR data in ppm, mp in °C. |
|---|---|---|---|---|
| 3.01 | Ethyl | Tetrahydropyran-3-yl | — | |
| 3.02 | Propyl | Tetrahydropyran-3-yl | — | |
| 3.03 | Ethyl | Tetrahydropyran-4-yl | — | |
| 3.04 | Propyl | Tetrahydropyran-4-yl | — | |
| 3.05 | Ethyl | Tetrahydrothiopyran-3-yl | — | |
| 3.06 | Propyl | Tetrahydrothiopyran-3-yl | — | |
| 3.07 | Ethyl | Tetrahydropyran-3-yl | 4-F | |
| 3.08 | Propyl | Tetrahydropyran-3-yl | 4-F | |
| 3.09 | Ethyl | Tetrahydropyran-4-yl | 4-F | |
| 3.10 | Propyl | Tetrahydropyran-4-yl | 4-F | |
| 3.11 | Ethyl | Tetrahydrothiopyran-3-yl | 4-F | |
| 3.12 | Propyl | Tetrahydrothiopyran-3-yl | 4-F | |
| 3.13 | Ethyl | Tetrahydropyran-3-yl | 4-Cl | |
| 3.14 | Propyl | Tetrahydropyran-3-yl | 4-Cl | |
| 3.15 | Ethyl | Tetrahydropyran-4-yl | 4-Cl | 1.35(m, 3H), 4.05–4.30(m, 2H), 4.60(m, 1H), 6.80–7.40(m, 4H) |
| 3.16 | Propyl | Tetrahydropyran-4-yl | 4-Cl | 1.35(m, 3H), 4.05–4.30(m, 2H), 4.60(m, 1H), 6.80–7.40(m, 4H) |
| 3.17 | Ethyl | Tetrahydrothiopyran-3-yl | 4-Cl | 1.35(m, 3H), 4.05–4.25(m, 2H), 4.60(m, 1H), 6.80–7.40(m, 4H) |
| 3.18 | Propyl | Tetrahydrothiopyran-3-yl | 4-Cl | 1.35(m, 3H), 4.05–4.30(m, 2H), 4.60(m, 1H), 6.80–7.40(m, 4H) |

TABLE D

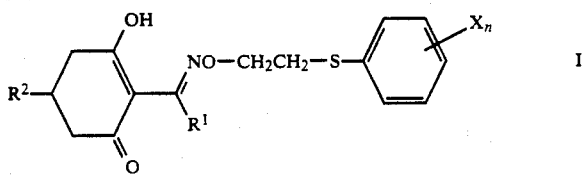

(A = —CH$_2$CH$_2$—S—; Z = Phenyl)

| No. | R$^1$ | R$^2$ | X$_n$ | Phys. data/NMR data in ppm, mp in °C. |
|---|---|---|---|---|
| 4.01 | Ethyl | Tetrahydropyran-3-yl | — | 3.90(m, 2H), 4.23(t, 2H), 7.17–7.43(m, 5H) |
| 4.02 | Propyl | Tetrahydropyran-3-yl | — | 65 |
| 4.03 | Ethyl | Tetrahydropyran-4-yl | — | 3.97(m, 2H), 4.23(t, 2H), 7.17–7.43(m, 5H) |
| 4.04 | Propyl | Tetrahydropyran-4-yl | — | 3.97(m, 2H), 4.23(t, 2H), 7.17–7.43(m, 5H) |
| 4.05 | Ethyl | Tetrahydrothiopyran-3-yl | — | 4.23(t, 2H), 7.17–7.43(m, 5H) |
| 4.06 | Propyl | Tetrahydrothiopyran-3-yl | — | 4.23(t, 2H), 7.17–7.43(m, 5H) |
| 4.07 | Ethyl | Tetrahydropyran-3-yl | 4-F | 3.90(m, 2H), 4.17(t, 2H), 7.00(m, 2H), 7.40(m, 2H) |
| 4.08 | Propyl | Tetrahydropyran-3-yl | 4-F | 3.90(m, 2H), 4.17(t, 2H), 7.00(m, 2H), 7.40(m, 2H) |
| 4.09 | Ethyl | Tetrahydropyran-4-yl | 4-F | 4.00(m, 2H), 4.17(t, 2H), 7.00(m, 2H), 7.40(m, 2H) |
| 4.10 | Propyl | Tetrahydropyran-4-yl | 4-F | 4.00(m, 2H), 4.17(t, 2H), 7.00(m, 2H), 7.40(m, 2H) |
| 4.11 | Ethyl | Tetrahydrothiopyran-3-yl | 4-F | 4.17(t, 2H), 7.00(m, 2H), 7.40(m, 2H), |
| 4.12 | Propyl | Tetrahydrothiopyran-3-yl | 4-F | 4.17(t, 2H), 7.00(m, 2H), 7.40(m, 2H), |
| 4.13 | Ethyl | Tetrahydropyran-3-yl | 4-Cl | 71–75 |
| 4.14 | Propyl | Tetrahydropyran-3-yl | 4-Cl | 63–65 |
| 4.15 | Ethyl | Tetrahydropyran-4-yl | 4-Cl | 4.00(m, 2H), 4.20(t, 2H), 7.30(m, 4H) |
| 4.16 | Propyl | Tetrahydropyran-4-yl | 4-Cl | 4.00(m, 2H), 4.20(t, 2H), 7.30(m, 4H) |
| 4.17 | Ethyl | Tetrahydrothiopyran-3-yl | 4-Cl | 4.20(t, 2H), 7.30(m, 4H) |
| 4.18 | Propyl | Tetrahydrothiopyran-3-yl | 4-Cl | 4.20(t, 2H), 7.30(m, 4H) |
| 4.19 | Ethyl | Tetrahydropyran-3-yl | 2-Cl | 3.90(m, 2H), 4.25(t, 2H), 7.10–7.50(m, 4H) |
| 4.20 | Propyl | Tetrahydropyran-3-yl | 2-Cl | 3.90(m, 2H), 4.25(t, 2H), 7.10–7.50(m, 4H) |
| 4.21 | Ethyl | Tetrahydropyran-4-yl | 2-Cl | 4.00(m, 2H), 4.25(t, 2H), 7.10–7.50(m, 4H) |
| 4.22 | Propyl | Tetrahydropyran-4-yl | 2-Cl | 4.00(m, 2H), 4.25(t, 2H) 7.10–7.50(m, 4H) |
| 4.23 | Ethyl | Tetrahydrothiopyran-3-yl | 2-Cl | 4.25(t, 2H)7.10–7.50(m, 4H) |
| 4.24 | Propyl | Tetrahydrothiopyran-3-yl | 2-Cl | 4.25(t, 2H)7.10–7.50(m, 4H) |

TABLE D-continued $$\text{structure: R}^2\text{-substituted cyclohexenone with OH, =NO-CH}_2\text{CH}_2\text{-S-phenyl-X}_n, \text{R}^1 \quad \text{I}$$

(A = —CH₂CH₂—S—; Z = Phenyl)

| No. | R¹ | R² | X$_n$ | Phys. data/NMR data in ppm, mp in °C. |
|---|---|---|---|---|
| 4.25 | Ethyl | Tetrahydropyran-3-yl | 2,6-Cl₂ | 3.90(m, 2H)4.20(t, 2H), 7.20(t, 1H) 7.40(d, 2H) |
| 4.26 | Propyl | Tetrahydropyran-3-yl | 2,6-Cl₂ | 3.90(m, 2H)4.20(t, 2H), 7.20(t, 1H) 7.40(d, 2H) |
| 4.27 | Ethyl | Tetrahydropyran-4-yl | 2,6-Cl₂ | 61–64 |
| 4.28 | Propyl | Tetrahydropyran-4-yl | 2,6-Cl₂ | 4.00(m, 2H)4.20(t, 2H), 7.20(t, 1H) 7.40(d, 2H) |
| 4.29 | Ethyl | Tetrahydrothiopyran-3-yl | 2,6-Cl₂ | 4.20(t, 2H)7.20(t, 2H), 7.40(d, 2H) |
| 4.30 | Propyl | Tetrahydrothiopyran-3-71 | 2,6-Cl₂ | 4.20(t, 2H)7.20(t, 2H), 7.40(d, 2H) |

TABLE E $$\text{structure: R}^2\text{-substituted cyclohexenone with OH, =NO-CH}_2\text{CH}_2\text{CH}_2\text{-O-phenyl-X}_n, \text{R}^1 \quad \text{I}$$

(A = —CH₂CH₂—CH₂O—; Z = Phenyl)

| No. | R¹ | R² | X$_n$ | Phys. data/NMR data in ppm, mp in °C. |
|---|---|---|---|---|
| 5.01 | Ethyl | Tetrahydropyran-3-yl | — | 3.90(m, 2H), 4.03(t, 2H), 4.23(t, 2H), 6.90(m, 3H), 7.27(m, 2H) |
| 5.02 | Propyl | Tetrahydropyran-3-yl | — | 3.90(m, 2H), 4.03(t, 2H), 4.23(t, 2H), 6.90(m, 3H), 7.27(m, 2H) |
| 5.03 | Ethyl | Tetrahydropyran-4-yl | — | 3.97(m, 2H), 4.03(t, 2H), 4.23(t, 2H), 6.90(m, 3H), 7.27(m, 2H) |
| 5.04 | Propyl | Tetrahydropyran-4-yl | — | 3.97(m, 2H), 4.03(t, 2H), 4.23(t, 2H), 6.90(m, 3H), 7.27(m, 2H) |
| 5.05 | Ethyl | Tetrahydrothiopyran-3-yl | — | 4.03(t, 2H), 4.23(t, 2H), 6.90(m, 3H), 7.27(m, 2H) |
| 5.06 | Propyl | Tetrahydrothiopyran-3-yl | — | 4.03(t, 2H), 4.23(t, 2H), 6.90(m, 3H), 7.27(m, 2H) |
| 5.07 | Ethyl | Tetrahydropyran-3-yl | 2-F | 3.90(m, 2H), 4.10(t, 2H), 4.27(t, 2H), 6.80–7.15(m, 4H) |
| 5.08 | Propyl | Tetrahydropyran-3-yl | 2-F | 3.90(m, 2H), 4.10(t, 2H), 4.27(t, 2H), 6.80–7.15(m, 4H) |
| 5.09 | Ethyl | Tetrahydropyran-4-yl | 2-F | 4.00(m, 2H), 4.10(t, 2H), 4.27(t, 2H), 6.80–7.15(m, 4H) |
| 5.10 | Propyl | Tetrahydropyran-4-yl | 2-F | 76–80 |
| 5.11 | Ethyl | Tetrahydrothiopyran-3-yl | 2-F | 4.10(t, 2H), 4.27(t, 2H), 6.80–7.15(m, 4H), |
| 5.12 | Propyl | Tetrahydrothiopyran-3-yl | 2-F | 4.10(t, 2H), 4.27(t, 2H), 6.80–7.15(m, 4H), |
| 5.13 | Ethyl | Tetrahydropyran-3-yl | 3-F | 3.90(m, 2H), 4.05(t, 2H), 4.27(t, 2H), 6.67(m, 3H), 7.23(m, 1H) |
| 5.14 | Propyl | Tetrahydropyran-3-yl | 3-F | 3.90(m, 2H), 4.05(t, 2H), 4.27(t, 2H), 6.67(m, 3H), 7.23(m, 1H) |
| 5.15 | Ethyl | Tetrahydropyran-4-yl | 3-F | 3.90–4.10(m, 4H), 4.27(t, 2H), 6.67(m, 3H), 7.23(m, 1H) |
| 5.16 | Propyl | Tetrahydropyran-4-yl | 3-F | 3.90–4.10(m, 4H), 4.27(t, 2H), 6.67(m, 3H), 7.23(m, 1H) |
| 5.17 | Ethyl | Tetrahydrothiopyran-3-yl | 3-F | 4.05(t, 2H), 4.27(t, 2H), 6.67(m, 3H) 7.23(m, 1H) |
| 5.18 | Propyl | Tetrahydrothiopyran-3-yl | 3-F | 4.05(t, 2H), 4.27(t, 2H), 6.67(m, 3H) 7.23(m, 1H) |
| 5.19 | Ethyl | Tetrahydropyran-3-yl | 4-F | 3.90(m, 2H), 4.03(t, 2H), 4.27(t, 2H), 6.90(m, 2H), 7.00(m, 2H) |
| 5.20 | Propyl | Tetrahydropyran-3-yl | 4-F | 3.90(m, 2H), 4.03(t, 2H), 4.27(t, 2H), 6.90(m, 2H), 7.00(m, 2H) |
| 5.21 | Ethyl | Tetrahydropyran-4-yl | 4-F | 3.90–4.06(m, 4H), 4.23(t, 2H), 6.90(m, 2H), 7.00(m, 2H) |
| 5.22 | Propyl | Tetrahydropyran-4-yl | 4-F | 3.90–4.06(m, 4H), 4.28(t, 2H), 6.90(m, 2H), 7.00(m, 2H) |
| 5.23 | Ethyl | Tetrahydrothiopyran-3-yl | 4-F | 4.03(t, 2H), 4.27(t, 2H), 6.90(m, 2H), 7.00(m, 2H) |
| 5.24 | Propyl | Tetrahydrothiopyran-3-yl | 4-F | 4.03(t, 2H), 4.27(t, 2H), 6.90(m, 2H), 7.00(m, 2H) |

TABLE E-continued

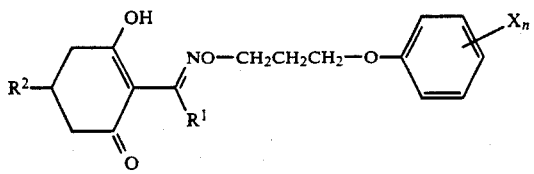

(A = —CH$_2$CH$_2$—CH$_2$O—; Z = Phenyl)

| No. | R$^1$ | R$^2$ | X$_n$ | Phys. data/NMR data in ppm, mp in °C. |
|---|---|---|---|---|
| 5.25 | Ethyl | Tetrahydropyran-3-yl | 2-Cl | |
| 5.26 | Propyl | Tetrahydropyran-3-yl | 2-Cl | |
| 5.27 | Ethyl | Tetrahydropyran-4-yl | 2-Cl | |
| 5.28 | Propyl | Tetrahydropyran-4-yl | 2-Cl | |
| 5.29 | Ethyl | Tetrahydrothiopyran-3-yl | 2-Cl | |
| 5.30 | Propyl | Tetrahydrothiopyran-3-yl | 2-Cl | |
| 5.31 | Ethyl | Tetrahydropyran-3-yl | 3-Cl | 3.90(m, 2H), 4.06(t, 2H), 4.27(t, 2H), 6.77(m, 1H), 6.90(m, 2H), 7.17(m, 1H) |
| 5.32 | Propyl | Tetrahydropyran-3-yl | 3-Cl | 3.90(m, 2H), 4.06(t, 2H), 4.27(t, 2H), 6.77(m, 1H), 6.90(m, 2H), 7.17(m, 1H) |
| 5.33 | Ethyl | Tetrahydropyran-4-yl | 3-Cl | 3.90–4.10(m, 4H), 4.27(t, 2H), 6.77(m, 1H), 6.90(m, 2H), 7.17(m, 1H) |
| 5.34 | Propyl | Tetrahydropyran-4-yl | 3-Cl | 3.90–4.10(m, 4H), 4.27(t, 2H), 6.77(m, 1H), 6.90(m, 2H), 7.17(m, 1H) |
| 5.35 | Ethyl | Tetrahydrothiopyran-3-yl | 3-Cl | 4.06(t, 2H), 4.27(t, 2H), 6.77(m, 1H), 6.90(m, 2H), 7.17(m, 1H) |
| 5.36 | Propyl | Tetrahydrothiopyran-3-yl | 3-Cl | 4.06(t, 2H), 4.27(t, 2H), 6.77(m, 1H), 6.90(m, 2H), 7.17(m, 1H) |
| 5.37 | Ethyl | Tetrahydropyran-3-yl | 4-Cl | 3.90(m, 2H), 4.03(t, 2H), 4.23(t, 2H), 6.80(m, 2H), 7.20(m, 2H) |
| 5.38 | Propyl | Tetrahydropyran-3-yl | 4-Cl | 3.90(m, 2H), 4.03(t, 2H), 4.23(t, 2H), 6.80(m, 2H), 7.20(m, 2H) |
| 5.39 | Ethyl | Tetrahydropyran-4-yl | 4-Cl | 3.90–4.09(m, 4H), 4.23(t, 2H), 6.80(m, 2H), 7.20(m, 2H) |
| 5.40 | Propyl | Tetrahydropyran-4-yl | 4-Cl | 3.90–4.09(m, 4H), 4.23(t, 2H), 6.80(m, 2H), 7.20(m, 2H) |
| 5.41 | Ethyl | Tetrahydrothiopyran-3-yl | 4-Cl | 4.03(t, 2H), 4.23(t, 2H), 6.80(m, 2H), 7.20(m, 2H) |
| 5.42 | Propyl | Tetrahydrothiopyran-3-yl | 4-Cl | 4.03(t, 2H), 4.23(t, 2H), 6.80(m, 2H), 7.20(m, 2H) |
| 5.43 | Ethyl | Tetrahydropyran-3-yl | 4-NO$_2$ | 3.90(m, 2H), 4.20(t, 2H), 4.28(t, 2H), 6.93(d, 2H), 8.20(d, H) |
| 5.44 | Propyl | Tetrahydropyran-3-yl | 4-NO$_2$ | 3.90(m, 2H), 4.20(t, 2H), 4.28(t, 2H), 6.93(d, 2H), 8.20(d, 2H) |
| 5.45 | Ethyl | Tetrahydropyran-4-yl | 4-NO$_2$ | 4.00(m, 2H), 4.20(t, 2H), 4.28(t, 2H), 6.93(d, 2H), 8.20(d, 2H) |
| 5.46 | Propyl | Tetrahydropyran-4-yl | 4-NO$_2$ | 4.00(m, 2H), 4.20(t, 2H), 4.28(t, 2H), 6.93(d, 2H), 8.20(d, 2H) |
| 5.47 | Ethyl | Tetrahydrothiopyran-3-yl | 4-NO$_2$ | 4.20(t, 2H), 4.28(t, 2H), 6.93(d, 2H), 8.20(d, 2H) |
| 5.48 | Propyl | Tetrahydrothiopyran-3-yl | 4-NO$_2$ | 4.20(t, 2H), 4.28(t, 2H), 6.93(d, 2H), 8.20(d, 2H) |
| 5.49 | Ethyl | Tetrahydropyran-3-yl | 4-Br | 3.90(m, 2H), 4.00(t, 2H), 4.27(t, 2H), 6.80(d, 2H), 7.37(d, 2H) |
| 5.50 | Propyl | Tetrahydropyran-3-yl | 4-Br | 3.90(m, 2H), 4.00(t, 2H), 4.27(t, 2H), 6.80(d, 2H), 7.37(d, 2H) |
| 5.51 | Ethyl | Tetrahydropyran-4-yl | 4-Br | 3.90–4.10(m, 4H), 4.27(t, 2H), 6.80(d, 2H), 7.37(d, 2H) |
| 5.52 | Propyl | Tetrahydropyran-4-yl | 4-Br | 3.90–4.10(m, 4H), 4.27(t, 2H), 6.80(d, 2H), 7.37(d, 2H) |
| 5.53 | Ethyl | Tetrahydrothiopyran-4-yl | 4-Br | 4.00(t, 2H), 4.27(t, 2H), 6.80(d, 2H), 7.37(d, 2H) |
| 5.54 | Propyl | Tetrahydrothiopyran-4-yl | 4-Br | 4.00(t, 2H), 4.27(t, 2H), 6.80(d, 2H), 7.37(d, 2H) |

TABLE F

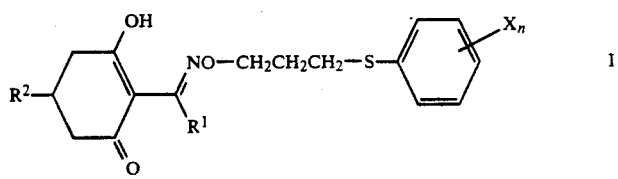

(A = —CH₂CH₂CH₂—S—; Z = Phenyl)

| No. | R¹ | R² | Xₙ | Phys. data/NMR data in ppm, mp in °C. |
|---|---|---|---|---|
| 6.01 | Ethyl | Tetrahydropyran-3-yl | — | 3.90(m, 2H), 4.17(t, 2H), 7.10–7.40(m, 5H) |
| 6.02 | Propyl | Tetrahydropyran-3-yl | — | 3.90(m, 2H), 4.17(t, 2H), 7.10–7.40(m, 5H) |
| 6.03 | Ethyl | Tetrahydropyran-4-yl | — | 4.00(m, 2H), 4.17(t, 2H), 7.10–7.40(m, 5H) |
| 6.04 | Propyl | Tetrahydropyran-4-yl | — | 4.00(m, 2H), 4.17(t, 2H), 7.10–7.40(m, 5H) |
| 6.05 | Ethyl | Tetrahydrothiopyran-3-yl | — | 4.17(t, 2H), 7.10–7.40(m, 5H) |
| 6.06 | Propyl | Tetrahydrothiopyran-3-yl | — | 4.17(t, 2H), 7.10–7.40(m, 5H) |
| 6.07 | Ethyl | Tetrahydropyran-3-yl | 4-F | 3.90(m, 2H), 4.17(t, 2H), 7.00(t, 2H), 7.33(m, 2H) |
| 6.08 | Propyl | Tetrahydropyran-3-yl | 4-F | 3.90(m, 2H), 4.17(t, 2H), 7.00(t, 2H), 7.33(m, 2H) |
| 6.09 | Ethyl | Tetrahydropyran-4-yl | 4-F | 4.00(m, 2H), 4.17(t, 2H), 7.00(t, 2H), 7.33(m, 2H) |
| 6.10 | Propyl | Tetrahydropyran-4-yl | 4-F | 4.00(m, 2H), 4.17(t, 2H), 7.00(t, 2H), 7.33(m, 2H) |
| 6.11 | Ethyl | Tetrahydrothiopyran-3-yl | 4-F | 4.17(t, 2H), 7.00(t, 2H), 7.33(m, 2H) |
| 6.12 | Propyl | Tetrahydrothiopyran-3-yl | 4-F | 4.17(t, 2H), 7.00(t, 2H), 7.33(m, 2H) |
| 6.13 | Ethyl | Tetrahydropyran-3-yl | 4-Cl | 3.90(m, 2H), 4.17(t, 2H), 7.27(s, 4H) |
| 6.14 | Propyl | Tetrahydropyran-3-yl | 4-Cl | 3.90(m, 2H), 4.17(t, 2H), 7.27(s, 4H) |
| 6.15 | Ethyl | Tetrahydropyran-4-yl | 4-Cl | 4.00(m, 2H), 4.17(t, 2H), 7.27(s, 4H) |
| 6.16 | Propyl | Tetrahydropyran-4-yl | 4-Cl | 4.00(m, 2H), 4.17(t, 2H), 7.27(s, 4H) |
| 6.17 | Ethyl | Tetrahydrothiopyran-3-yl | 4-Cl | 4.17(t, 2H), 7.27(s, 4H) |
| 6.18 | Propyl | Tetrahydrothiopyran-3-yl | 4-Cl | 4.17(t, 2H), 7.27(s, 4H) |
| 6.19 | Ethyl | Tetrahydropyran-3-yl | 2-Cl | 3.90(m, 2H), 4.20(t, 2H), 7.07–7.40(m, 4H) |
| 6.20 | Propyl | Tetrahydropyran-3-yl | 2-Cl | 3.90(m, 2H), 4.20(t, 2H), 7.07–7.40(m, 4H) |
| 6.21 | Ethyl | Tetrahydropyran-4-yl | 2-Cl | 4.00(m, 2H), 4.20(t, 2H), 7.07–7.40(m, 4H) |
| 6.22 | Propyl | Tetrahydropyran-4-yl | 2-Cl | 4.00(m, 2H), 4.20(t, 2H), 7.07–7.40(m, 4H) |
| 6.23 | Ethyl | Tetrahydrothiopyran-3-yl | 2-Cl | 4.20(t, 2H), 7.07–7.40(m, 4H) |
| 6.24 | Propyl | Tetrahydrothiopyran-3-yl | 2-Cl | 4.20(t, 2H), 7.07–7.40(m, 4H) |
| 6.25 | Ethyl | Tetrahydropyran-3-yl | 3-Cl | 3.90(m, 2H), 4.20(t, 2H), 7.17(m, 3H) 7.30(m, 1H) |
| 6.26 | Propyl | Tetrahydropyran-3-yl | 3-Cl | 3.90(m, 2H), 4.20(t, 2H), 7.17(m, 3H) 7.30(m, 1H) |
| 6.27 | Ethyl | Tetrahydropyran-4-yl | 3-Cl | 4.00(m, 2H), 4.20(t, 2H), 7.17(m, 3H) 7.30(m, 1H) |
| 6.28 | Propyl | Tetrahydropyran-4-yl | 3-Cl | 4.00(m, 2H), 4.20(t, 2H), 7.17(m, 3H) 7.30(m, 1H) |
| 6.29 | Ethyl | Tetrahydrothiopyran-3-yl | 3-Cl | 4.20(t, 2H), 7.17(m, 3H), 7.30(m, 1H) |
| 6.30 | Propyl | Tetrahydrothiopyran-3-yl | 3-Cl | 4.20(t, 2H), 7.17(m, 3H), 7.30(m, 1H) |
| 6.31 | Ethyl | Tetrahydropyran-3-yl | 2,5-Cl₂ | 3.90(m, 2H), 4.20(t, 2H), 7.07(dd, 1H), 7.20(d, 1H), 7.30(d, 1H) |
| 6.32 | Propyl | Tetrahydropyran-3-yl | 2,5-Cl₂ | 3.90(m, 2H), 4.20(t, 2H), 7.07(dd, 1H), 7.20(d, 1H), 7.30(d, 1H) |
| 6.33 | Ethyl | Tetrahydropyran-4-yl | 2,5-Cl₂ | 4.00(m, 2H), 4.20(t, 2H), 7.07(dd, 1H), 7.20(d, 1H)7.30(d, 1H) |
| 6.34 | Propyl | Tetrahydropyran-4-yl | 2,5-Cl₂ | 4.00(m, 2H), 4.20(t, 2H), 7.07(dd, 1H), 7.20(d, 1H)7.30(d, 1H) |
| 6.35 | Ethyl | Tetrahydrothiopyran-3-yl | 2,5-Cl₂ | 4.20(t, 2H), 7.07(dd, 1H), 7.20(d, 1H) 7.30(d, 1H) |
| 6.36 | Propyl | Tetrahydrothiopyran-3-yl | 2,5-Cl₂ | 4.20(t, 2H), 7.07(dd, 1H), 7.20(d, 1H) 7.30(d, 1H) |
| 6.37 | Ethyl | Tetrahydropyran-3-yl | 2,6-Cl₂ | 3.90(m, 2H), 4.20(t, 2H), 7.20(t, 1H) 7.40(d, 2H) |
| 6.38 | Propyl | Tetrahydropyran-3-yl | 2,6-Cl₂ | 3.90(m, 2H), 4.20(t, 2H), 7.20(t, 1H) 7.40(d, 2H) |
| 6.39 | Ethyl | Tetrahydropyran-4-yl | 2,6-Cl₂ | 4.00(m, 2H), 4.20(t, 2H), 7.20(t, 1H) 7.40(d, 2H) |
| 6.40 | Propyl | Tetrahydropyran-4-yl | 2,6-Cl₂ | 4.00(m, 2H), 4.20(t, 2H), 7.20(t, 1H) 7.40(d, 2H) |
| 6.41 | Ethyl | Tetrahydrothiopyran-3-yl | 2,6-Cl₂ | 4.20(t, 2H), 7.20(t, 1H), 7.40(d, 2H) |
| 6.42 | Propyl | Tetrahydrothiopyran-3-yl | 2,6-Cl₂ | 4.20(t, 2H), 7.20(t, 1H), 7.40(d, 2H) |

TABLE G

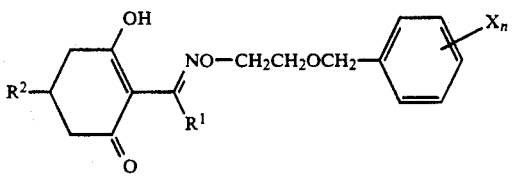

(A = —CH$_2$CH$_2$—O—CH$_2$—; Z = Phenyl)

| No. | R$^1$ | R$^2$ | X$_n$ | Phys. data/NMR data in ppm, mp in °C. |
|---|---|---|---|---|
| 7.01 | Ethyl | Tetrahydropyran-3-yl | — | 3.90(m, 2H), 4.25(t, 2H), 4.58(s, 2H), 7.38(s, 5H) |
| 7.02 | Propyl | Tetrahydropyran-3-yl | — | 3.90(m, 2H)4.25(t, 2H), 4.58(2, 2H), 7.38(s, 5H) |
| 7.03 | Ethyl | Tetrahydropyran-4-yl | — | 4.03(m, 2H), 4.33(m, 2H), 4.60(s, 2H), 7.40(s, 5H) |
| 7.04 | Propyl | Tetrahydropyran-4-yl | — | 4.03(m, 2H), 4.33(m, 2H), 4.60(s, 2H), 7.40(s, 5H) |
| 7.05 | Ethyl | Tetrahydrothiopyran-3-yl | — | 4.27(m, 2H), 4.57(s, 2H), 7.35(s, 5H) |
| 7.06 | Propyl | Tetrahydrothiopyran-3-yl | — | 4.27(m, 2H), 4.57(s, 2H), 7.35(s, 5H) |
| 7.07 | Ethyl | Tetrahydropyran-3-yl | 2-F | 3.93(m, 2H), 4.27(m, 2H), 4.67(s, 2H), 6.93–7.50(m, 4H) |
| 7.08 | Propyl | Tetrahydropyran-3-yl | 2-F | 3.93(m, 2H), 4.27(m, 2H), 4.67(s, 2H), 6.93–7.50(m, 4H) |
| 7.09 | Ethyl | Tetrahydropyran-4-yl | 2-F | 4.03(m, 2H), 4.27(m, 2H), 4.63(s, 2H), 6.97–7.50(m, 4H) |
| 7.10 | Propyl | Tetrahydropyran-4-yl | 2-F | 4.03(m, 2H), 4.27(m, 2H), 4.63(s, 2H), 6.97–7.50(m, 4H) |
| 7.11 | Ethyl | Tetrahydrothiopyran-3-yl | 2-F | 4.27(m, 2H), 4.67(s, 2H), 6.97–7.50(m, 4H) |
| 7.12 | Propyl | Tetrahydrothiopyran-3-yl | 2-F | 4.27(m, 2H), 4.67(s, 2H), 6.97–7.50(m, 4H) |
| 7.13 | Ethyl | Tetrahydroyran-3-yl | 3-F | 3.93(m, 2H), 4.27(m, 2H), 4.57(s, 2H), 6.90–7.15(m, 3H), 7.23–7.40(m, 1H) |
| 7.14 | Propyl | Tetrahydroyran-3-yl | 3-F | 3.93(m, 2H), 4.27(m, 2H), 4.57(s, 2H), 6.90–7.15(m, 3H), 7.23–7.40(m, 1H) |
| 7.15 | Ethyl | Tetrahydropyran-4-yl | 3-F | 4.03(m, 2H), 4.25(m, 2H), 4.60(s, 2H), 6.90–7.18(m, 3H), 7.26–7.40(m, 1H) |
| 7.16 | Propyl | Tetrahydropyran-4-yl | 3-F | 4.03(m, 2H), 4.25(m, 2H), 4.60(s, 2H), 6.90–7.18(m, 3H), 7.26–7.40(m, 1H) |
| 7.17 | Ethyl | Tetrahydrothiopyran-3-yl | 3-F | 4.27(m, 2H), 4.60(s, 2H), 6.90–7.15(m, 3H), 7.23–7.40(m, 1H) |
| 7.18 | Propyl | Tetrahydrothiopyran-3-yl | 3-F | 4.27(m, 2H), 4.60(s, 2H), 6.90–7.15(m, 3H), 7.23–7.40(m, 1H) |
| 7.19 | Ethyl | Tetrahydropyran-3-yl | 4-F | 3.93(m, 2H), 4.23(m, 2H), 4.53(s, 2H), 7.00(m, 2H), 7.30(m, 2H) |
| 7.20 | Propyl | Tetrahydropyran-3-yl | 4-F | 3.93(m, 2H), 4.23(m, 2H), 4.53(s, 2H), 7.00(m, 2H), 7.30(m, 2H) |
| 7.21 | Ethyl | Tetrahydropyran-4-yl | 4-F | 92 |
| 7.22 | Propyl | Tetrahydropyran-4-yl | 4-F | 4.00(m, 2H), 4.23(m, 2H), 4.53(s, 2H), 7.03(m, 2H), 7.30(m, 2H) |
| 7.23 | Ethyl | Tetrahydrothiopyran-3-yl | 4-F | 4.27(m, 2H), 4.53(s, 2H), 7.03(m, 2H), 7.30(m, 2H) |
| 7.24 | Propyl | Tetrahydrothiopyran-3-yl | 4-F | 4.27(m, 2H), 4.53(s, 2H), 7.03(m, 2H), 7.30(m, 2H) |
| 7.25 | Ethyl | Tetrahydropyran-3-yl | 2-Cl | |
| 7.26 | Propyl | Tetrahydropyran-3-yl | 2-Cl | |
| 7.27 | Ethyl | Tetrahydropyran-4-yl | 2-Cl | |
| 7.28 | Propyl | Tetrahydropyran-4-yl | 2-Cl | |
| 7.29 | Ethyl | Tetrahydrothiopyran-3-yl | 2-Cl | |
| 7.30 | Propyl | Tetrahydrothiopyran-3-yl | 2-Cl | |
| 7.31 | Ethyl | Tetrahydropyran-3-yl | 3-Cl | |
| 7.32 | Propyl | Tetrahydropyran-3-yl | 3-Cl | |
| 7.33 | Ethyl | Tetrahydropyran-4-yl | 3-Cl | |
| 7.34 | Propyl | Tetrahydropyran-4-yl | 3-Cl | |
| 7.35 | Ethyl | Tetrahydrothiopyran-3-yl | 3-Cl | |
| 7.36 | Propyl | Tetrahydrothiopyran-3-yl | 3-Cl | |
| 7.37 | Ethyl | Tetrahydropyran-3-yl | 4-Cl | 3.93(m, 2H), 4.27(m, 2H), 4.53(s, 2H), 7.28(m, 4H) |
| 7.38 | Propyl | Tetrahydropyran-3-yl | 4-Cl | 3.93(m, 2H), 4.27(m, 2H), 4.53(s, 2H), 7.28(m, 4H) |
| 7.39 | Ethyl | Tetrahydropyran-4-yl | 4-Cl | 67–72 |
| 7.40 | Propyl | Tetrahydropyran-4-yl | 4-Cl | 4.00(m, 2H), 4.23(m, 2H), 4.53(s, 2H), 7.28(m, 4H) |
| 7.41 | Ethyl | Tetrahydrothiopyran-3-yl | 4-Cl | 4.27(m, 2H), 4.53(s, 2H), 7.28(m, 4H) |
| 7.42 | Propyl | Tetrahydrothiopyran-3-yl | 4-Cl | 4.27(m, 2H), 4.53(s, 2H), 7.28(m, 4H) |
| 7.43 | Ethyl | Tetrahydropyran-3-yl | 2-CH$_3$ | 3.93(m, 2H), 4.23(m, 2H), 4.57(s, 2H), 7.09–7.33(m, 4H) |
| 7.44 | Propyl | Tetrahydropyran-3-yl | 2-CH$_3$ | 3.93(m, 2H), 4.23(m, 2H), 4.57(s, 2H), 7.09–7.33(m, 4H) |

TABLE G-continued

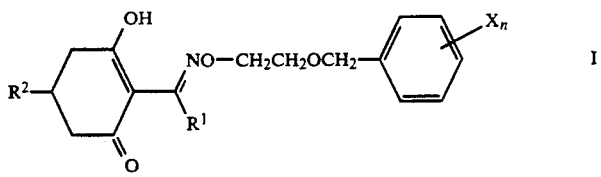

(A = —CH$_2$CH$_2$—O—CH$_2$—; Z = Phenyl)

| No. | R$^1$ | R$^2$ | X$_n$ | Phys. data/NMR data in ppm, mp in °C. |
|---|---|---|---|---|
| 7.45 | Ethyl | Tetrahydropyran-4-yl | 2-CH$_3$ | 4.00(m, 2H), 4.23(m, 2H), 4.57(s, 2H), 7.09–7.33(m, 4H) |
| 7.46 | Propyl | Tetrahydropyran-4-yl | 2-CH$_3$ | 4.00(m, 2H), 4.23(m, 2H), 4.57(s, 2H), 7.09–7.33(m, 4H) |
| 7.47 | Ethyl | Tetrahydrothiopyran-3-yl | 2-CH$_3$ | 4.23(m, 2H), 4.57(s, 2H), 7.09–7.33(m, 4H) |
| 7.48 | Propyl | Tetrahydrothiopyran-3-yl | 2-CH$_3$ | 4.23(m, 2H), 4.57(s, 2H), 7.09–7.33(m, 4H) |
| 7.49 | Ethyl | Tetrahydropyran-3-yl | 3-CH$_3$ | 3.93(m, 2H), 4.25(m, 2H), 4.57(s, 2H), 7.00–7.32(m, 4H) |
| 7.50 | Propyl | Tetrahydropyran-3-yl | 3-CH$_3$ | 3.93(m, 2H), 4.25(m, 2H), 4.57(s, 2H), 7.00–7.32(m, 4H) |
| 7.51 | Ethyl | Tetrahydropyran-4-yl | 3-CH$_3$ | 4.00(m, 2H), 4.27(m, 2H), 4.57(s, 2H), 7.00–7.32(m, 4H) |
| 7.52 | Propyl | Tetrahydropyran-4-yl | 3-CH$_3$ | 4.00(m, 2H), 4.27(m, 2H), 4.57(s, 2H), 7.00–7.32(m, 4H) |
| 7.53 | Ethyl | Tetrahydrothiopyran-3-yl | 3-CH$_3$ | 4.27(m, 2H), 4.60(s, 2H), 7.00–7.32(m, 4H) |
| 7.54 | Propyl | Tetrahydrothiopyran-3-yl | 3-CH$_3$ | 4.27(m, 2H), 4.60(s, 2H), 7.00–7.32(m, 4H) |
| 7.55 | Ethyl | Tetrahydropyran-3-yl | 4-CH$_3$ | 3.93(m, 2H), 4.20(m, 2H), 4.53(s, 2H), 7.07–7.30(m, 4H) |
| 7.56 | Propyl | Tetrahydropyran-3-yl | 4-CH$_3$ | 3.93(m, 2H), 4.20(m, 2H), 4.53(s, 2H), 7.07–7.30(m, 4H) |
| 7.57 | Ethyl | Tetrahydropyran-4-yl | 4-CH$_3$ | 4.00(m, 2H), 4.23(m, 2H), 4.57(s, 2H), 7.03–7.27(m, 4H) |
| 7.58 | Propyl | Tetrahydropyran-4-yl | 4-CH$_3$ | 4.00(m, 2H), 4.23(m, 2H), 4.57(s, 2H), 7.03–7.27(m, 4H) |
| 7.59 | Ethyl | Tetrahydrothiopyran-3-yl | 4-CH$_3$ | 4.23(m, 2H), 4.57(s, 2H), 7.07–7.30(m, 4H) |
| 7.60 | Propyl | Tetrahydrothiopyran-3-yl | 4-CH$_3$ | 4.28(m, 2H), 4.57(s, 2H), 7.07–7.30(m, 4H) |
| 7.61 | Ethyl | Tetrahydropyran-3-yl | 4-tert.-C$_4$H$_9$ | 3.93(m, 2H), 4.23(m, 2H), 4.53(s, 2H), 7.20–7.40(m, 4H) |
| 7.62 | Propyl | Tetrahydropyran-3-yl | 4-tert.-C$_4$H$_9$ | 3.93(m, 2H), 4.23(m, 2H), 4.53(s, 2H), 7.20–7.40(m, 4H) |
| 7.63 | Ethyl | Tetrahydropyran-4-yl | 4-tert.-C$_4$H$_9$ | 4.00(m, 2H), 4.23(m, 2H), 4.53(s, 2H), 7.20–7.40(m, 4H) |
| 7.64 | Propyl | Tetrahydropyran-4-yl | 4-tert.-C$_4$H$_9$ | 4.00(m, 2H), 4.23(m, 2H), 4.53(s, 2H), 7.20–7.40(m, 4H) |
| 7.65 | Ethyl | Tetrahydrothiopyran-3-yl | 4-tert.-C$_4$H$_9$ | 4.23(m, 2H), 4.53(s, 2H), 7.20–7.40(m, 4H) |
| 7.66 | Propyl | Tetrahydrothiopyran-3-yl | 4-tert.-C$_4$H$_9$ | 4.23(m, 2H), 4.53(s, 2H), 7.20–7.40(m, 4H) |

TABLE H

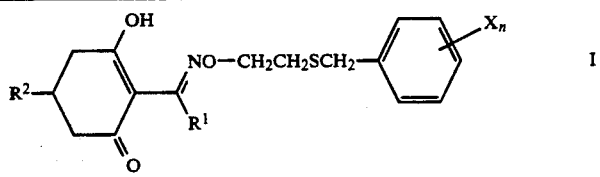

(A = —CH$_2$CH$_2$—S—CH$_2$—; Z = Phenyl)

| No. | R$^1$ | R$^2$ | X$_n$ | Phys. data/NMR data in ppm, mp in °C. |
|---|---|---|---|---|
| 8.01 | Ethyl | Tetrahydropyran-3-yl | — | 3.73(s, 2H), 3.90(m, 2H), 4.17(t, 2H), 728(s, 5H) |
| 8.02 | Propyl | Tetrahydropyran-3-yl | — | 3.73(s, 2H), 3.90(m, 2H), 4.17(t, 2H), 728(s, 5H) |
| 8.03 | Ethyl | Tetrahydropyran-4-yl | — | 3.77(s, 2H), 4.00(m, 2H), 4.13(t, 2H), 7.28(s, 5H) |
| 8.04 | Propyl | Tetrahydropyran-4-yl | — | 3.77(s, 2H), 4.00(m, 2H), 4.13(t, 2H), 7.28(s, 5H) |
| 8.05 | Ethyl | Tetrahydrothiopyran-3-yl | — | 3.80(s, 2H), 4.13(t, 2H), 7.28(s, 5H) |
| 8.06 | Propyl | Tetrahydrothiopyran-3-yl | — | 3.80(s, 2H), 4.13(t, 2H), 7.28(s, 5H) |

TABLE H-continued

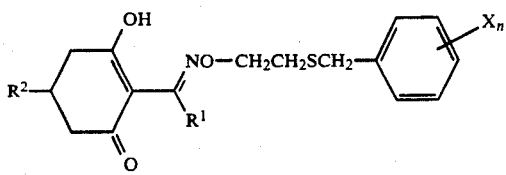

(A = —CH₂CH₂—S—CH₂—; Z = Phenyl)

| No. | R¹ | R² | Xₙ | Phys. data/NMR data in ppm, mp in °C. |
|---|---|---|---|---|
| 8.07 | Ethyl | Tetrahydropyran-3-yl | 4-F | 3.72(s, 2H), 3.90(m, 2H), 4.13(t, 2H), 7.00(m, 2H), 7.30(m, 2H) |
| 8.08 | Propyl | Tetrahydropyran-3-yl | 4-F | 3.72(s, 2H), 3.90(m, 2H), 4.13(t, 2H), 7.00(m, 2H), 7.30(m, 2H) |
| 8.09 | Ethyl | Tetrahydropyran-4-yl | 4-F | 63–65 |
| 8.10 | Propyl | Tetrahydropyran-4-yl | 4-F | 3.73(s, 2H), 4.00(m, 2H), 4.13(t, 2H), 7.00(m, 2H), 7.30(m, 2H) |
| 8.11 | Ethyl | Tetrahydrothiopyran-3-yl | 4-F | 3.75(s, 2H), 4.13(t, 2H), 7.00(m, 2H), 7.30(m, 2H) |
| 8.12 | Propyl | Tetrahydrothiopyran-3-yl | 4-F | 3.75(s, 2H), 4.13(t, 2H), 7.00(m, 2H), 7.30(m, 2H) |
| 8.13 | Ethyl | Tetrahydropyran-3-yl | 4-Cl | 3.77(s, 2H), 3.93(m, 2H), 4.13(t, 2H), 7.30(s, 4H) |
| 8.14 | Propyl | Tetrahydropyran-3-yl | 4-Cl | 3.77(s, 2H), 3.93(m, 2H), 4.13(t, 2H), 7.30(s, 4H) |
| 8.15 | Ethyl | Tetrahydropyran-4-yl | 4-Cl | 3.73(s, 2H), 4.00(m, 2H), 4.17(t, 2H), 7.30(s, 4H) |
| 8.16 | Propyl | Tetrahydropyran-4-yl | 4-Cl | 3.73(s, 2H), 4.00(m, 2H), 4.17(t, 2H), 7.30(s, 4H) |
| 8.17 | Ethyl | Tetrahydrothiopyran-3-yl | 4-Cl | 3.73(s, 2H), 4.13(m, 2H), 7.30(s, 4H) |
| 8.18 | Propyl | Tetrahydrothiopyran-3-yl | 4-Cl | 3.73(s, 2H), 4.13(m, 2H), 7.30(s, 4H) |

TABLE I

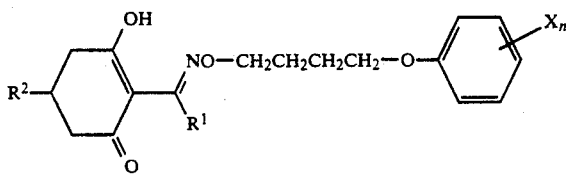

(A = —CH₂CH₂CH₂CH₂—O—; Z = Phenyl)

| No. | R¹ | R² | Xₙ | Phys. data/NMR data in ppm, mp in °C. |
|---|---|---|---|---|
| 9.01 | Ethyl | Tetrahydropyran-3-yl | — | 3.70–4.20(m, 6H), 6.90(m, 3H), 7.30(m, 2H) |
| 9.02 | Propyl | Tetrahydropyran-3-yl | — | 3.70–4.20(m, 6H), 6.90(m, 3H), 7.30(m, 2H) |
| 9.03 | Ethyl | Tetrahydropyran-4-yl | — | 3.83–4.23(m, 6H), 6.90(m, 3H), 7.30(m, 2H) |
| 9.04 | Propyl | Tetrahydropyran-4-yl | — | 3.83–4.23(m, 6H), 6.90(m, 3H), 7.30(m, 2H) |
| 9.05 | Ethyl | Tetrahydrothiopyran-3-yl | — | 4.00(bs, 2H), 4.13(bs, 2H), 6.90(m, 3H) 7.30(m, 2H) |
| 9.06 | Propyl | Tetrahydrothiopyran-3-yl | — | 4.00(bs, 2H), 4.13(bs, 2H), 6.90(m, 3H) 7.30(m, 2H) |
| 9.07 | Ethyl | Tetrahydropyran-3-yl | 2-F | 3.93(m, 2H), 4.00–4.20(m, 4H), 6.80–7.15(m, 4H) |
| 9.08 | Propyl | Tetrahydropyran-3-yl | 2-F | 3.93(m, 2H), 4.00–4.20(m, 4H), 6.80–7.15(m, 4H) |
| 9.09 | Ethyl | Tetrahydropyran-4-yl | 2-F | 68–72 |
| 9.10 | Propyl | Tetrahydropyran-4-yl | 2-F | 3.90–4.20(m, 6H), 6.80–7.15(m, 4H) |
| 9.11 | Ethyl | Tetrahydrothiopyran-3-yl | 2-F | 4.00–4.20(m, 4H), 6.80–7.15(m, 4H) |
| 9.12 | Propyl | Tetrahydrothiopyran-3-yl | 2-F | 4.00–4.20(m, 4H), 6.80–7.15(m, 4H) |
| 9.13 | Ethyl | Tetrahydropyran-3-yl | 3-F | |
| 9.14 | Propyl | Tetrahydropyran-3-yl | 3-F | |
| 9.15 | Ethyl | Tetrahydropyran-4-yl | 3-F | |
| 9.16 | Propyl | Tetrahydropyran-4-yl | 3-F | |
| 9.17 | Ethyl | Tetrahydrothiopyran-3-yl | 3-F | |
| 9.18 | Propyl | Tetrahydrothiopyran-3-yl | 3-F | |
| 9.19 | Ethyl | Tetrahydropyran-3-yl | 4-F | 3.80–4.20(m, 6H), 6.75–7.05(m, 4H) |
| 9.20 | Propyl | Tetrahydropyran-3-yl | 4-F | 3.80–4.20(m, 6H), 6.75–7.05(m, 4H) |
| 9.21 | Ethyl | Tetrahydropyran-4-yl | 4-F | 3.90–4.20(m, 6H), 6.75–7.05(m, 4H) |
| 9.22 | Propyl | Tetrahydropyran-4-yl | 4-F | 3.90–4.20(m, 6H), 6.75–7.05(m, 4H) |
| 9.23 | Ethyl | Tetrahydrothiopyran-3-yl | 4-F | 3.90–4.20(m, 4H), 6.75–7.05(m, 4H) |
| 9.24 | Propyl | Tetrahydrothiopyran-3-yl | 4-F | 3.90–4.20(m, 4H), 6.75–7.05(m, 4H) |
| 9.25 | Ethyl | Tetrahydropyran-3-yl | 4-Cl | 3.80–4.20(m, 6H), 6.80(m, 2H), |

TABLE I-continued

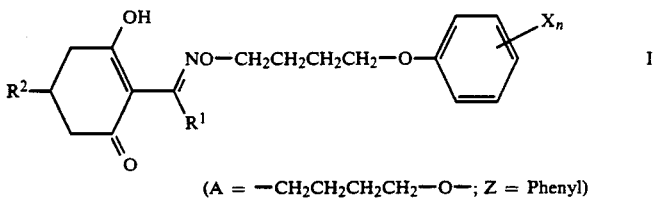

(A = —CH₂CH₂CH₂CH₂—O—; Z = Phenyl)

| No. | R¹ | R² | X$_n$ | Phys. data/NMR data in ppm, mp in °C. |
|---|---|---|---|---|
| 9.26 | Propyl | Tetrahydropyran-3-yl | 4-Cl | 3.80–4.20(m, 6H), 6.80(m, 2H), 7.20(m, 2H) |
| 9.27 | Ethyl | Tetrahydropyran-4-yl | 4-Cl | 3.90–4.20(m, 6H), 6.80(m, 2H), 7.20(m, 2H) |
| 9.28 | Propyl | Tetrahydropyran-4-yl | 4-Cl | 3.90–4.20(m, 6H), 6.80(m, 2H), 7.20(m, 2H) |
| 9.29 | Ethyl | Tetrahydrothiopyran-3-yl | 4-Cl | 3.90–4.20(m, 4H), 6.80(m, 2H), 7.20(m, 2H) |
| 9.30 | Propyl | Tetrahydrothiopyran-3-yl | 4-Cl | 3.90–4.20(m, 4H), 6.80(m, 2H), 7.20(m, 2H) |
| 9.31 | Ethyl | Tetrahydropyran-3-yl | 2,6-Cl₂ | 3.93(m, 2H), 4.00–4.25(m, 4H), 7.00(t, 1H), 7.30(d, 2H) |
| 9.32 | Propyl | Tetrahydropyran-3-yl | 2,6-Cl₂ | 3.93(m, 2H), 4.00–4.25(m, 4H), 7.00(t, 1H), 7.30(d, 2H) |
| 9.33 | Ethyl | Tetrahydropyran-4-yl | 2,6-Cl₂ | 3.90–4.25(m, 6H), 7.00(t, 1H), 7.30(d, 2H) |
| 9.34 | Propyl | Tetrahydropyran-4-yl | 2,6-Cl₂ | 3.90–4.25(m, 6H), 7.00(t, 1H), 7.30(d, 2H) |
| 9.35 | Ethyl | Tetrahydrothiopyran-3-yl | 2,6-Cl₂ | 4.00–4.20(m, 4H), 7.00(t, 1H), 7.30(d, 2H) |
| 9.36 | Propyl | Tetrahydrothiopyran-3-yl | 2,6-Cl₂ | 4.00–4.20(m, 4H), 7.00(t, 1H), 7.30(d, 2H) |

TABLE J

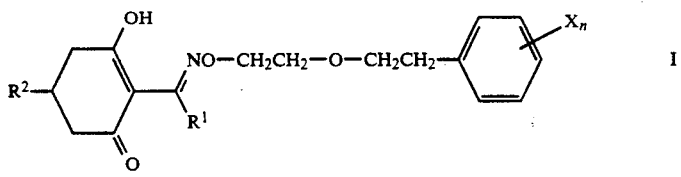

(A = —CH₂CH₂—O—CH₂CH₂—; Z = Phenyl)

| No. | R¹ | R² | X$_n$ | Phys. data/NMR data in ppm, mp in °C. |
|---|---|---|---|---|
| 10.01 | Ethyl | Tetrahydropyran-3-yl | — | 3.90(m, 2H), 4.20(m, 2H), 7.25(m, 5H) |
| 10.02 | Propyl | Tetrahydropyran-3-yl | — | 3.90(m, 2H), 4.20(m, 2H), 7.25(m, 5H) |
| 10.03 | Ethyl | Tetrahydropyran-4-yl | — | |
| 10.04 | Propyl | Tetrahydropyran-4-yl | — | |
| 10.05 | Ethyl | Tetrahydrothiopyran-3-yl | — | 4.20(m, 2H), 7.25(m, 5H) |
| 10.06 | Propyl | Tetrahydrothiopyran-3-yl | — | 4.20(m, 2H), 7.25(m, 5H) |
| 10.07 | Ethyl | Tetrahydropyran-3-yl | 4-F | 3.90(m, 2H), 4.17(m, 2H), 6.93(m, 2H), 7.13(m, 2H) |
| 10.08 | Propyl | Tetrahydropyran-3-yl | 4-F | 3.90(m, 2H), 4.17(m, 2H), 6.93(m, 2H), 7.13(m, 2H) |
| 10.09 | Ethyl | Tetrahydropyran-4-yl | 4-F | |
| 10.10 | Propyl | Tetrahydropyran-4-yl | 4-F | |
| 10.11 | Ethyl | Tetrahydrothiopyran-3-yl | 4-F | 4.17(m, 2H), 6.93(m, 2H), 7.13(m, 2H) |
| 10.12 | Propyl | Tetrahydrothiopyran-3-yl | 4-F | 4.17(m, 2H), 6.93(m, 2H), 7.13(m, 2H) |
| 10.13 | Ethyl | Tetrahydropyran-3-yl | 4-Cl | 3.90(m, 2H), 4.17(m, 2H), 7.13(m, 4H) |
| 10.14 | Propyl | Tetrahydropyran-3-yl | 4-Cl | 3.90(m, 2H), 4.17(m, 2H), 7.13(m, 4H) |
| 10.15 | Ethyl | Tetrahydropyran-4-yl | 4-Cl | |
| 10.16 | Propyl | Tetrahydropyran-4-yl | 4-Cl | |
| 10.17 | Ethyl | Tetrahydrothiopyran-3-yl | 4-Cl | 4.17(m, 2H), 7.13(m, 4H) |
| 10.18 | Propyl | Tetrahydrothiopyran-3-yl | 4-Cl | 4.17(m, 2H), 7.13(m, 4H) |

TABLE K

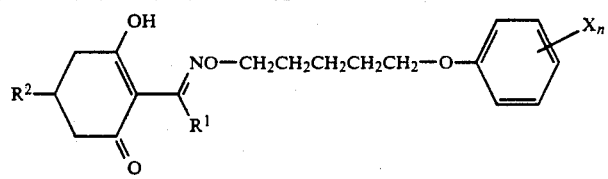

(A = —CH$_2$(CH$_2$)$_3$CH$_2$—O—; Z = Phenyl)

| No. | R$^1$ | R$^2$ | X$_n$ | Phys. data/NMR data in ppm, mp in °C. |
|---|---|---|---|---|
| 11.01 | Ethyl | Tetrahydropyran-3-yl | — | 3.80–4.17(m, 6H), 6.90(m, 3H), 7.27(m, 2H) |
| 11.02 | Propyl | Tetrahydropyran-3-yl | — | 3.80–4.17(m, 6H), 6.90(m, 3H), 7.27(m, 2H) |
| 11.03 | Ethyl | Tetrahydropyran-4-yl | — | 3.90–4.17(m, 6H), 6.90(m, 3H), 7.27(m, 2H) |
| 11.04 | Propyl | Tetrahydropyran-4-yl | — | 3.90–4.17(m, 6H), 6.90(m, 3H), 7.27(m, 2H) |
| 11.05 | Ethyl | Tetrahydrothiopyran-3-yl | — | 3.97(t, 2H), 4.07(t, 2H), 6.90(m, 3H), 7.27(m, 2H) |
| 11.06 | Propyl | Tetrahydrothiopyran-3-yl | — | 3.97(t, 2H), 4.07(t, 2H), 6.90(m, 3H), 7.27(m, 2H) |
| 11.07 | Ethyl | Tetrahydropyran-3-yl | 4-F | 3.90(m, 4H), 4.03(t, 2H), 6.70–7.03(m, 4H) |
| 11.08 | Propyl | Tetrahydropyran-3-yl | 4-F | 3.90(m, 4H), 4.03(t, 2H), 6.70–7.03(m, 4H) |
| 11.09 | Ethyl | Tetrahydropyran-4-yl | 4-F | 3.83–4.13(m, 6H), 6.70–7.03(m, 4H) |
| 11.10 | Propyl | Tetrahydropyran-4-yl | 4-F | 3.83–4.13(m, 6H), 6.70–7.03(m, 4H) |
| 11.11 | Ethyl | Tetrahydrothiopyran-3-yl | 4-F | 3.90(t, 2H), 4.03(t, 2H)6.70–7.03(m, 4H) |
| 11.12 | Propyl | Tetrahydrothiopyran-3-yl | 4-F | 3.90(t, 2H), 4.03(t, 2H)6.70–7.03(m, 4H) |
| 11.13 | Ethyl | Tetrahydropyran-3-yl | 4-Cl | 3.80–4.10(m, 6H), 6.80(d, 2H), 7.20(d, 2H) |
| 11.14 | Propyl | Tetrahydropyran-3-yl | 4-Cl | 3.80–4.10(m, 6H), 6.80(d, 2H), 7.20(d, 2H) |
| 11.15 | Ethyl | Tetrahydropyran-4-yl | 4-Cl | 3.87–4.10(m, 6H), 6.80(d, 2H), 7.20(d, 2H) |
| 11.16 | Propyl | Tetrahydropyran-4-yl | 4-Cl | 3.87–4.10(m, 6H), 6.80(d, 2H), 7.20(d, 2H) |
| 11.17 | Ethyl | Tetrahydrothiopyran-3-yl | 4-Cl | 54–61 |
| 11.18 | Propyl | Tetrahydrothiopyran-3-yl | 4-Cl | 3.90(t, 2H), 4.07(t, 2H), 6.80(d, 2H) 7.20(d, 2H) |

USE EXAMPLES

The action of the cyclohexenone derivatives of the formula I on plant growth is demonstrated in greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for postemergence treatment was 0.25 kg/ha.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the experiments were *Oryza sativa*, *Setaria italica* and *Setaria viridis*.

Compounds 7.21 and 7.23, applied postemergence at a rate of 0.25 kg/ha, combated unwanted grassy plants very well, and were at the same time tolerated by rice as an example of a crop plant.

We claim:

1. A cyclohexenone oxime ether of the formula I

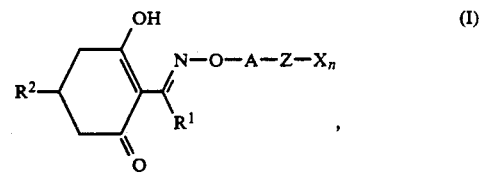

where
R$^1$ is C$_1$–C$_6$-alkyl;
A is an unsubstituted or C$_1$–C$_3$-alkyl-substituted C$_3$–C$_6$-alkylene or C$_4$–C$_6$-alkenylene chain in which a methylene group is replaced by an oxygen atom, a sulfur atom, a sulfoxyl group, a sulfonyl group or —N(R$^q$)—, where
R$^a$ is hydrogen, C$_1$–C$_4$-alkyl, C$_3$–C$_6$-alkenyl or C$_3$–C$_6$-alkynyl,
Z is phenyl,
    a 5-membered heteroaromatic structure having from one to three heteroatoms selected from the group consisting of three nitrogen atoms and an oxygen or a sulfur atom, or
    a 6-membered heteroaromatic structure having from one to four nitrogen atoms,
X is an amino group —NR$^q$R$^b$, where $R^a$ is hydrogen, $C_1-C_4$-alkyl, $C_3-C_6$-alkenyl or $C_3-C_6$-alkynyl and $R^b$ is hydrogen, $C_1-C_4$-alkyl, $C_3-C_6$-alkenyl, $C_3-C_6$-alkynyl, $C_1-C_6$-acyl or benzoyl, where the aromatic ring may carry from one to three substituents selected from the group consisting of nitro, cyano, halogen, $C_1-C_4$-alkyl, $C_1-C_4$-alkoxy, $C_1-C_4$-alkylthio and $C_1-C_4$-haloalkyl;

nitro, cyano, halogen, $C_1-C_4$-alkyl, partially or completely halogenated $C_1-C_4$-alkyl, $C_1-C_4$-alkoxy, $C_1-C_4$-alkylthio, partially or completely halogenated $C_1-C_4$-alkoxy, carboxyl, $C_1-C_4$-alkoxycarbonyl, benzyloxycarbonyl or phenyl, where the aromatic radicals may additionally carry from one to three of the followsubstituents: nitro, cyano, halogen, $C_1-C_4$-alkyl, partially or completely halogenated $C_1-C_4$-alkyl, $C_1-C_4$-alkoxy, $C_1-C_4$-alkylthio, partially or completely halogenated $C_1-C_4$-alkoxy, carboxyl, $C_1-C_4$-alkoxycarbonyl or benzyloxycarbonyl;

n is from 0 to 3 or 1 to 5 where Z is halogen;

$R^2$ is $C_1-C_4$-alkoxy-$C_1-C_6$-alkyl- or $C_1-C_4$-alkylthio-$C_1-C_6$-alkyl;

$C_3-C_7$-cycloalkyl or $C_5-C_7$-cycloalkenyl, where these groups may carry from one to three substituents selected from the group consisting of $C_1-C_4$-alkyl, $C_1-C_4$-alkoxy, $C_1-C_4$-alkylthio, partially or completely halogenated $C_1-C_4$-alkyl, hydroxyl and halogen;

a 5-membered saturated heterocyclic structure containing one or two heteroatoms selected from the group consisting of oxygen and sulfur, where the heterocyclic structure may additionally carry from one to three radicals selected from the group consisting of $C_1-C_4$-alkyl, $C_1-C_4$-alkoxy, $C_1-C_4$-alkylthio and partially or completely halogenated $C_1-C_4$-alkyl;

a 6- or 7-membered saturated or mono- or diunsaturated heterocyclic structure containing one or two heteroatoms selected from the group consisting of oxygen and sulfur, where the heterocyclic structure may additionally carry from one to three radicals selected from the group consisting of hydroxy, halogen, $C_1-C_4$-alkyl, $C_1-C_4$-alkoxy, $C_1-C_4$-alkylthio and partially or completely halogenated $C_1-C_4$-alkyl;

a 5-membered heteroaromatic structure containing one to three heteroatoms selected from the group consisting of two nitrogen atoms and an oxygen or a sulfur atom, where this ring may additionally contain from one to three radicals selected from the group consisting of halogen, cyano, $C_1-C_4$-alkyl, $C_1-C_4$-alkoxy, $C_1-C_4$-alkylthio, partially or completely halogenated $C_1-C_4$-alkyl, $C_2-C_6$-alkenyl, $C_2-C_6$-alkenyloxy, partially or completely halogenated $C_2-C_6$-alkenyl and $C_1-C_4$-alkoxy-$C_1-C_4$-alkyl;

phenyl or pyridyl, where these groups may additionally carry from one to three radicals selected from the group consisting of halogen, nitro, cyano, $C_1-C_4$-alkyl, $C_1-C_4$-alkoxy, $C_1-C_4$-alkylthio, partially or completely halogenated $C_1-C_4$-Alkyl, $C_3-C_6$-alkenyloxy, $C_3-C_6$-alkynyloxy and —$NR^aR^b$, where $R^a$ and $R^b$ have the above meanings, and their agriculturally useful salts and esters of $C_1-C_{10}$-carboxylic acids and inorganic acids.

2. Cyclohexenone oxime ethers of the formula I as set forth in claim 1, where Z is phenyl.

3. A herbicidal composition containing inert additives and a herbicidally effective amount of at least one compound of the formula I as set forth in claim 1.

4. A process for combating the growth of unwanted plants, wherein the unwanted plants and/or their habitat are treated with a herbicidally effective amount of a cyclohexenone derivative of the formula I as set forth in claim 1.

5. A cyclohexenone oxime ether of the formula I as set forth in claim 1, wherein $R^2$ is tetrahydropyran and Z is phenyl.

6. A herbicidal composition comprising inert additives and a herbicidally effective amount of at least one compound of the formula I as set forth in claim 5.

7. A process for combatting the growth of unwanted plants which comprises: treating the unwanted plants and/or their habitat with a herbicidally effective amount of a compound of the formula I as set forth in claim 5.

* * * * *

UNITED STATES PATENT AND TRADEMARK OFFICE
CERTIFICATE OF CORRECTION

PATENT NO. : 5,190,573

DATED : March 2, 1993

INVENTOR(S) : MISSLITZ et al.

It is certified that error appears in the above-identified patent and that said Letters Patent is hereby corrected as shown below:

Column 1, line 53, "Z" should read "X".

Claim 1, column 61, line 21, "Z" should read "X".

Signed and Sealed this

Twenty-third Day of November, 1993

*Attest:*

BRUCE LEHMAN

*Attesting Officer*  *Commissioner of Patents and Trademarks*